(12) United States Patent
Hama et al.

(10) Patent No.: US 7,591,575 B2
(45) Date of Patent: Sep. 22, 2009

(54) LIGHT EMITTING DEVICE

(75) Inventors: Atsutomo Hama, Anan (JP); Junji Takeichi, Anan (JP); Takafumi Sugiyama, Anan (JP); Yukihiro Hayashi, Anan (JP)

(73) Assignee: Nichia Corporation, Anan-shi (JP)

( * ) Notice: Subject to any disclaimer, the term of this patent is extended or adjusted under 35 U.S.C. 154(b) by 99 days.

(21) Appl. No.: 12/016,803

(22) Filed: Jan. 18, 2008

(65) Prior Publication Data

US 2008/0117620 A1 May 22, 2008

Related U.S. Application Data

(63) Continuation of application No. 11/306,106, filed on Dec. 16, 2005, now Pat. No. 7,356,054.

(30) Foreign Application Priority Data

| Dec. 17, 2004 | (JP) | ............................. | 2004-366645 |
| Feb. 8, 2005 | (JP) | ............................. | 2005-032189 |
| Mar. 10, 2005 | (JP) | ............................. | 2005-066459 |
| Mar. 24, 2005 | (JP) | ............................. | 2005-085594 |
| Mar. 30, 2005 | (JP) | ............................. | 2005-098064 |
| Apr. 25, 2005 | (JP) | ............................. | 2005-126193 |

(51) Int. Cl.
 *H01L 33/00* (2006.01)
(52) U.S. Cl. .................. 362/555; 362/231; 362/84; 362/551
(58) Field of Classification Search ................ 362/551, 362/555, 583, 572, 574, 575, 582, 617–618, 362/84; 313/512, 484; 385/125; 433/29
See application file for complete search history.

(56) References Cited

U.S. PATENT DOCUMENTS

| 3,131,690 | A | 5/1964 | Innis et al. | |
| 5,483,546 | A | 1/1996 | Johnson et al. | |
| 6,695,982 | B2 * | 2/2004 | Ellens et al. | .......... 252/301.4 S |
| 6,963,688 | B2 * | 11/2005 | Nath | .......................... 385/125 |
| 2002/0025901 | A1 * | 2/2002 | Ono et al. | .................... 501/119 |
| 2002/0038074 | A1 | 3/2002 | Hakamata | |
| 2003/0007087 | A1 | 1/2003 | Hakamata et al. | |
| 2005/0139813 | A1 | 6/2005 | Yamaguchi et al. | |
| 2005/0215861 | A1 | 9/2005 | Hakamata | |
| 2006/0023468 | A1 * | 2/2006 | Takahashi et al. | ........... 362/555 |

FOREIGN PATENT DOCUMENTS

WO   WO-01/40702  A1   6/2001

* cited by examiner

*Primary Examiner*—Ali Alavi
(74) *Attorney, Agent, or Firm*—Global IP Counselors, LLP

(57) ABSTRACT

The present invention provides a light emitting device comprising: an excitation light source which radiates excitation light; a wavelength converting member which absorbs and converts the wavelength of at least part of the excitation light radiated from the excitation light source, and releases light with a predetermined wavelength band; a light guide for guiding the excitation light radiated from the excitation light source to the wavelength converting member, with one end at the excitation light source and the other end at the wavelength converting member, wherein the refractive index of the cross-sectional center region (core) is higher than that of the circumferential region (clad); and a thermally conductive transparent film which contacts with the wavelength converting member.

4 Claims, 14 Drawing Sheets

(a)

(b)

LIGHT EMITTING DEVICE

CROSS-REFERENCE TO RELATED APPLICATIONS

This application is a continuation application of U.S. patent application Ser. No. 11/306,106 filed on Dec. 15, 2005. This application claims priority to Japanese Patent Application No. 2004-366645, 2005-032189, 2005-098064, 2005-066459, 2005-085594, and 2005-126193. The entire disclosures of U.S. patent application Ser. No. 11/306,106, Japanese Patent Application Nos. 2004-366645, 2005-032189, 2005-098064, 2005-066459, 2005-085594, and 2005-126193 are hereby incorporated herein by reference.

BACKGROUND OF THE INVENTION

1. Field of the Invention

The present invention relates to a light emitting device, and more particularly relates to light emitting device which has an excitation light source, a wavelength converting member, and a light guide.

2. Background Information

Conventionally, endoscope devices, fiber scopes and the like require a light which represents a high luminance and accurate reproduction of color information.

Therefore, the use of semiconductor light emitting elements such as light emitting diode elements (LED) and laser diode elements (LD) or the like have been proposed as light sources to replace xenon lamps or the like (for instance, JP 2002-95634-A and JP 2003-515899-A).

Semiconductor light emitting elements are compact, have good power efficiency, and emit brilliant colored light. Furthermore, these elements are formed from semiconductors, so there is no concern about burning out. In particular, semiconductor lasers emit light which has extremely high-intensity compared to that of light emitting diodes, and therefore can realize light sources with excellent illumination.

Generally, in order to be able to accurately reproduce color information using a semiconductor light emitting element, light of various wavelengths must be combined to obtain a white light.

Therefore, normally a wavelength converting member made from fluorescent material and resin or the like is used in combination with a semiconductor light emitting element.

However, the light density of semiconductor light emitting elements is extremely high, so the resin and fluorescent material or the like which make up the wavelength converting member will become hot and can be degraded. Therefore, there are problems where the life of the light emitting device is shortened or the light from the semiconductor light emitting element cannot be fully released to the outside.

Furthermore, a laser diode has a peak width at half height which is narrower than a light emitting diode, so conventional endoscope devices which use a laser diode to achieve a white light source may have problems such as color variation because of the different intensities of each laser diode, and poor color reproduction. Furthermore, a conventional endoscope device requires at least three types of laser diodes, so the output from each of the laser diodes must be controlled in order to obtain a predetermined white light, and there are problems with this adjustment being difficult. Furthermore, a laser diode has a narrower viewing angle than a light emitting diode, and the light emitting intensity is extremely high from the front, and therefore, even though the light is white, there may be problems with the color changing if the laser diode shifts position even slightly.

SUMMARY OF THE INVENTION

An object of the present invention is to provide a long-lasting light emitting device which uses semiconductor light emitting elements with good light emitting efficiency and prevents degradation of the members which compose the light emitting device.

From another viewpoint, an object of the present invention is to provide a high-performance light emitting device which can achieve high light emitting efficiency for emitting light at extremely high luminance.

The present invention provides a light emitting device comprising: an excitation light source which radiates excitation light; a wavelength converting member which absorbs and converts the wavelength of at least part of the excitation light radiated from the excitation light source, and releases light with a predetermined wavelength band; a light guide for guiding the excitation light radiated from the excitation light source to the wavelength converting member, with one end at the excitation light source and the other end at the wavelength converting member, wherein the refractive index of the cross-sectional center region (core) is higher than that of the circumferential region (clad); and a thermally conductive transparent film which contacts with the wavelength converting member.

Further, the present invention provides another light emitting device comprising: an excitation light source which radiates excitation light, a light guide which transfers excitation light radiated from the excitation light source, which flexibly extends in the longitudinal direction, and a wavelength converting member which absorbs and converts the wavelength of the excitation light radiated from the excitation light source through the light guide, and releases light with a predetermined wavelength band, wherein: the light guide has an end surface with a larger surface area than the lateral cross-sectional area orthogonal to the longitudinal direction on the excitation light radiating side, and is supported by a light guide end member; and at least a part of the light guide and light guide end member are covered by the wavelength converting member.

Moreover, the present invention provide still another light emitting device comprising: a light emitting element, a light guide with a light receiving end which receives light from the light emitting element and a radiating end which radiates, which flexibly extends, and a translucent member which transmits light radiated from the light guide, wherein: the light emitting device has a light guide end member which covers the side surface of the radiating end of the light guide and forms the sidewall of a concave part which has at least a part of the light guide radiating end as the bottom part; and the translucent member extends into the concave part.

According to the light emitting device of the present invention, a thermal conductive transparent film is provided which contacts the wavelength converting member, so heat generated in the wavelength converting member can easily and sufficiently be released and degradation caused by heating can effectively be prevented. In other words, normally fluorescent materials and the resins or the like which compose the wavelength converting member are degraded by the heat caused by heating of the excitation light source itself. However, with the light emitting device of the present invention, a high output excitation light source is used to continuously send high light density light, but the wavelength converting member can be established at a location some distance away from the excitation light source because of the use of the light guide. In addition, a thermally conductive transparent film which contacts the wavelength converting member is provided and thereby heat generated by the wavelength converting member is effectively removed through this film, and heating and degradation of the fluorescent material which compose the wavelength converting member can be prevented.

Furthermore, according to the light emitting device of the present invention, degradation caused by heating of the materials which compose the wavelength converting member can effectively be prevented and optical output can dramatically be increased. This is thought to be because of the synergistic effect that the light radiation side end surface of the light guide has an area larger than the cross-sectional area orthogonal to the longitudinal direction, so the light density is reduced, as well as that the heat generated in the wavelength converting member can effectively be released and at least part of the wavelength converted light is reflected by the end surface of the light guide end member because the wavelength converting member covers at least a part of the light guide end member.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
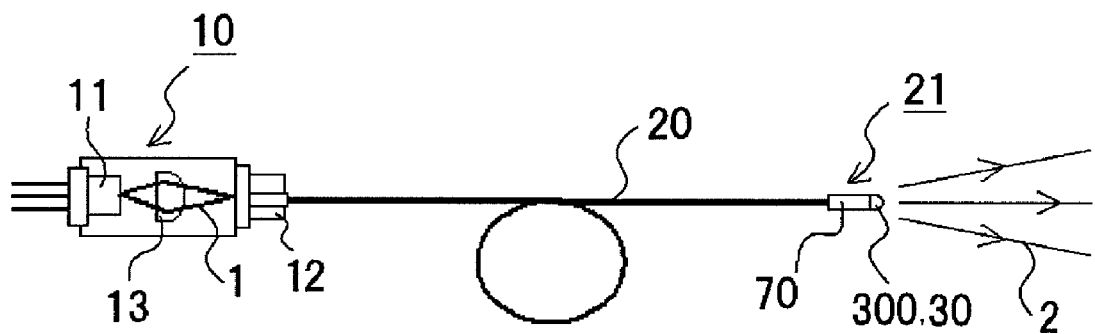
FIG. 1 is a schematic diagram for describing the unit structure for the light emitting device of the present invention.

As shown in FIG. 1, the light emitting device of the present invention is primarily comprised of, for instance, an excitation light source 10 (a light emitting element 1), a light guide 20, and a translucent member 300 (a wavelength converting member 30).

Excitation Light Source

As shown in FIG. 1, the excitation light source is comprised of light emitting elements 11 or the like, and is constructed such that the light radiated from the light emitting elements 11 is guided from the radiating part 12 to the light guide 20.

The excitation light source is a light source which emits excitation light. As the excitation light herein, any light may be used so long as the light can excite a fluorescent material to be discussed later. The excitation light source may use a device which is an energy source for the semiconductor light emitting elements, lamps or the like, as well as electron beams, plasma, and EL or the like. Of these, the use of semiconductor light emitting elements is preferable. Semiconductor light emitting elements make possible compact light emitting devices with good power efficiency because the light emitting intensity is high. Furthermore, a light emitting device can be obtained which has excellent initial drive properties and is robust against vibration or repeated on-off switching. Semiconductor light emitting elements may be light emitting diode elements (LED) or laser diode elements (LD) or the like, but of these, laser diode elements are preferable. These laser diode elements make possible light emitting devices which have extremely high light emitting output. For instance, a device which radiates light with a main light emitting peak wavelength of approximately 350 nm to 550 nm is preferable. Thereby, as will be discussed later, fluorescent materials with good wavelength converting efficiency can be used, and as a result, a light emitting device with high light emitting output can be obtained while obtaining light with a variety of colors. Furthermore, degradation of the wavelength converting member, which will be discussed later, can be prevented, and a light emitting device with long life and high reliability can be obtained.

The semiconductor light emitting element normally is constructed by laminating a semiconductor layer over a substrate.

As substrates, a sapphire substrate which has a C surface, R surface and A surface is preferably used in order to form a nitride semiconductor with good crystalline properties with high productivity. Furthermore, as is conventionally known, a nitride semiconductor may be grown on materials other than a nitride semiconductor that are capable of growing a nitride semiconductor, for instance, an insulative substrate such as spinel ($MgAl_2O_4$) which forms a main surface of any one of the C surface, R surface or A surface; SiC (including 6H, 4H, and 3C); ZnS; ZnO; GaAs; Si; GaN; and oxide substrates or the like which are lattice matched with a nitride semiconductor. In addition, the substrate may be off-angle, and in this case, the off-angle substrate preferably has one or more directions in a step configuration so that the base layer formed from gallium nitride can be grown with good crystalline properties.

If a different substrate from a nitride semiconductor is used, after growing the nitride semiconductor (buffer layer, base layer, or the like) which forms the base layer prior to forming the element structure on the different substrate from a nitride semiconductor, the different substrate may be removed by a method such as polishing to make a nitride semiconductor (such as GaN) with a single substrate, or the different substrate may be removed after forming the element structure.

By forming a base layer comprising a buffer layer (low temperature growth layer) and/or a nitride semiconductor (preferably GaN) or the like on a different substrate, the growth of the nitride semiconductor which composes the element structure will be favorable, and light in the ultraviolet band can be efficiently emitted by the pn junctions made from these nitride semiconductors.

A non-monocrystalline layer grown at low temperature, such as GaN, AlN, or GaAlN, or the like may be used as a buffer layer.

ELOG (epitaxially laterally overgrowth) growth may be used for the base layer (growth substrate) established on the different substrate. For instance, this can be achieved by optionally growing a nitride semiconductor layer on the different substrate and forming (to be nearly perpendicular to the orientation flat surface of the substrate) thereon a mask field with a stripe configuration or the like using a protective film (such as $SiO_2$ or the like) onto which a nitride semiconductor is not easily grown as well as forming a no-mask field for growing the nitride semiconductor such that the nitride semiconductor layer is grown over this protective layer. By growing the nitride semiconductor from the no-mask field, the nitride semiconductor will also growth in the mask field so that a nearly flat semiconductor layer can be formed by selective growth, or in other words, because growth in the lateral direction will occur in addition to growth in the film thickness direction. Alternatively, the same can be achieved by forming an opening region in the nitride semiconductor layer which has been grown on the different substrate and forming a nitride semiconductor layer on the substrate which includes this opening region. In other words, nitride semiconductor growth will occur in the lateral direction from the side surface of the opening region, and therefore a nearly flat semiconductor layer can be formed.

The semiconductor formed on this substrate may be any type of semiconductor including BN, SiC, ZnSe, GaN, InGaN, InAlGaN, AlGaN, BAlGaN, and BInAlGaN or the like. Similarly, Si, Zn, or the like may be added as an impurity element to the above elements to make a center of light emission.

In particular, nitride semiconductors, and especially Group III nitride semiconductors (such as nitride semiconductors containing Al and Ga, and nitride semiconductors containing In and Ga, $In_XAl_YGa_{1-x-y}N$, $0 \leq X$, $0 \leq Y$, $X+Y \leq 1$) are more suitable as light emitting layer materials which can efficiently emit light in a band from the ultraviolet band to a visible short wavelength band (for instance blue) where fluorescent materials can efficiently become excited. Furthermore, some of the gallium nitride compound type semiconductor may be replaced with B or P. The emission light wavelength from the light emitting element obtained can be adjusted by appropriately setting the types of semiconductor and the mixing ratio thereof. For instance, depending on the composition of the active layer, light which has a main emission peak wavelength between approximately 350 to 550 nm and preferably between approximately 350 to 500 nm or 360 to 500 nm can be obtained, and in particular, light which has a main emission peak wavelength within a range of 420 to 490 nm can be obtained by changing the In content of the active layer.

The semiconductor layer may have a single layer, but homostructures having MIS junctions, PIN junctions, or PN junctions or the like, heterostructures, and double heterostructures are preferably used. Furthermore, a multilayer laminate structure or an ultra lattice structure are also acceptable, as are a single quantum well structure or a multiquantum well structure laminated as a thin film which generates quantum effects.

The semiconductor layer may have a laminate double heterostructure or the like with a first contact layer of n-type gallium nitride, a first clad layer of n-type aluminum gallium nitride, a multiquantum well structure active layer with a plurality of lamination layers consisting of a well layer of indium nitride aluminum gallium or InGaN and a barrier layer of aluminum nitride gallium or GaN, a second clad layer of p-type aluminum nitride gallium, and a second contact layer of p-type gallium nitride, in order.

These semiconductor layers may be formed using a known technology such as Metal Organic Chemical Vapor Deposition (MOCVD), Hydride Vapor Phase Epitaxy (HVPE), or Molecular Beam Epitaxy (MBE) or the like. The film thickness of the semiconductor layer is not restricted in particular, and a variety of film thickness is can be used.

Incidentally, nitride semiconductors have n type conductivity without being doped with impurities. If n-type nitride semiconductors are formed in order to increase the light emitting efficiency or the like, Si, Ge, Se, Te, or C or the like are preferably introduced, as appropriate, as the n-type dopant. On the other hand, when forming a p-type nitride semiconductor, doping with a p-type dopant such as Zn, Mg, Be, Ca, Sr, or Ba or the like is preferable. For instance, impurity concentrations of approximately $10^{15}$ to $10^{21}/cm^3$ and particularly $10^{17}$ to $10^{20}/cm^3$ at the contact layer are exemplified. A nitride semiconductor is difficult to change to a p-type semiconductor simply by doping with a p-type dopant, so after introducing the p-type dopant, preferably the resistance is further dropped by annealing in a furnace or by plasma irradiation or the like.

For instance, an n-type contact layer which is an n-type nitride semiconductor layer, a crack preventing layer, an n-type clad layer, and an n-type light guide layer are formed on the substrate over an optional buffer layer. Excluding the n-type clad layer, the other layers can be omitted depending on the element. The n-type nitride semiconductor layer must have a bandgap which is wider than the active layer at least in the region which contacts the active layer, and therefore a composition which contains aluminum is preferable. For instance, an n-type $Al_yGa_{1-y}N$ ($0 \leq y < 1$) layer (value of y may be different for each layer) may be exemplified. Each layer may be grown while doping with an n-type impurity and made to be n-type, or maybe grown without doping and made to be n-type.

An active layer is formed over the n-type nitride semiconductor layer. The active layer preferably has an MQW structure wherein an $In_{x1}Al_{y1}Ga_{1-x1-y1}N$ well layer ($0 \leq x1 \leq 1$, $0 \leq y1 \leq 1$, $0 \leq x1+y1 \leq 1$) and an $In_{x2}Al_{y2}Ga_{1-x2-y2}N$ barrier layer ($0 \leq x2 \leq 1$, $0 \leq y2 \leq 1$, $0 \leq x2+y2 \leq 1$, $x1 > x2$) are repeatedly alternatingly layered an appropriate number of times in order of barrier layer/well layer/barrier layer. Normally barrier layers are on both sides of the active layer.

The well layer is formed undoped. On one hand, except for the final barrier layer adjacent to the p-type nitride semiconductor layer, all of the barrier layers are doped (preferably $1 \times 10^{17}$ to $1 \times 10^{19}/cm^3$), with an n-type impurity such as Si or Sn or the like, and the final barrier wall is grown undoped. Incidentally, p-type impurities such as Mg or the like from the adjacent p-type nitride semiconductor layer are diffused in the final barrier layer (for instance at a concentration of $1\times10^{16}$ to $1\times10^{19}/cm^3$). By doping n-type impurities into the barrier layers excluding the final barrier layer, the initial electron concentration in the active layer will be higher and electron injection efficiency to the well layers will also be higher, and the light emitting efficiency of the laser will be increased. On the other hand, the final barrier layer is closest to the p-type nitride semiconductor side and therefore does not contribute to injecting electrons to the well layer. Therefore, by not doping the final barrier layer with n-type impurities but rather essentially doping by diffusing p-type impurities from the p-type nitride semiconductor layer, the efficiency for hole injection into the well layer can be increased. Furthermore, by not doping the final barrier layer with n-type impurities, mixing of differing types of impurities in the barrier layer which reduces the mobility of the carrier can be prevented. When growing the final barrier layer, the growth may be performed while doping with p-type impurities such as Mg or the like at a concentration of $1\times10^{19}/cm^3$ or lower. In order to suppress the effect of decomposing the active layer which contains In by gas etching when growing the p-type nitride semiconductor, the final barrier layer is preferably formed to be thicker than the other barrier layers. For instance, a thickness between 1.1 and 10 times the other barrier layers is preferable and a thickness between 1.1 and 5 times the other barrier layers is more preferable.

A p-type electron containment layer, p-type light guide layer, p-type clad layer, and p-type contact layer are formed as a p-type nitride semiconductor layer on the final barrier layer. Except for the p-type clad layer, the other layers may be omitted depending on the element. The p-type nitride semiconductor layer must have a bandgap which is wider than the active layer at least in the region which contacts with the active layer, and therefore formulations which contain Al are preferable. For instance, a p-type $Al_zGa_{1-z}N$ ($0 \leq z < 1$) layer (the value of z may differ for each layer) may be exemplified. Thereby, a so-called double heterostructure is formed. Furthermore, each layer may be grown while doping with a p-type impurity to make p-type, and diffusing p-type impurities from other adjacent layers to make p-type is also acceptable.

The p-type electron containment layer is made from a p-type nitride semiconductor with an Al mixing ratio higher than that of the p-type clad layer, and preferably is formulated from $Al_xGa_{1-x}N$ ($0.1 < x < 0.5$). Furthermore, p-type impurities such as Mg or the like have a high concentration, and doping is preferably performed at a concentration of $5\times10^{17}$ to $1\times10^{19}/cm^3$. Therefore, the p-type electron containment layer can effectively contain electrons in the active layer, and the threshold value of the laser can be reduced. Furthermore, the p-type electron containment layer may be grown to a thin-film of approximately 30 to 200 Angstroms, and if thin, the film can be grown at temperatures lower than the p-type light guide layer or the p-type light clad layer. Therefore, by forming the p-type electron containment layer, decomposition of the active layer which contains In can be suppressed as compared to when directly forming the p-type light guide layer or the like on the active layer.

Furthermore, the semiconductor light emitting element may be a semiconductor laser element which has a ridge stripe being formed on the upper side of the active layer (partway to the p-type light guide layer), an active layer being between the guide layers and/or a resonator end face. Furthermore, a protective layer, p-electrode, n-electrode, p pad electrode and n pad electrode or the like may also be formed.

In particular, if the second electrode is formed on the second contact layer, the second electrode is preferably formed on nearly the whole surface as an ohmic electrode. Furthermore, the second electrode is preferably adjusted the sheet resistance as Rp>Rn in which Rp is the sheet resistance of the second electrode and Rn is the sheet resistance of the first contact layer, for instance the n-type contact layers. Normally, the n-type contact layer for instance is formed with a film thickness between 3 and 10 µm, and particularly between 4 and 6 µm, so the sheet resistance Rn is estimated to be between 10 and 15 ohms/square, and therefore a thin film is preferably formed so that Rp has a sheet resistance higher than this. Specifically, a range of 150 µm or more may be exemplified for the second electrode.

In this manner, when the p-type electrode and the n-type electrode have a relationship such that Rp>Rn, a p side pad electrode which has an extension conductor is preferably established on the p electrode in order to diffuse current across the whole p layer in order to efficiently emit the light from the whole active layer. Thereby the external quantum efficiency can be further increased. The shape of the extension conductor is not restricted in particular, and for instance may be linear, curved, lattice, branched, ancyroid, or mesh or the like. These configurations are preferable because the area which blocks the light can be reduced. The p side pad electrode has increased light shielding properties in comparison to the total area so the line width and length is preferably designed so that the light shielding effect is not stronger than the light emission enhancing effect.

Furthermore, the second electrode is preferably formed from a translucent material. For instance, a metallic or alloy single layer film or multilayer film which includes ITO, ZnO, $In_2O_3$, $SnO_2$, gold and one type element selected from platinum family elements may be exemplified. In particular, if the second electrode is formed from a multiple layer film or an alloy film made from a metallic or an alloy including at least one element selected from a group of gold and platinum family elements, and another type of element, the sheet resistance Rp of the p electrode can be adjusted depending on the content of gold or platinum family elements included therein, and therefore the stability and reproducibility of the electrode can be improved. However, gold and platinum elements have high absorption values in the 300 to 550 nm wavelength band, so the transparency can be improved by reducing the content thereof. The relationship between Rp and Rn can be determined by the condition of the light intensity distribution when the light emitting element is emitting light.

If an insulating substrate is used, a laser element made from a nitride semiconductor can be formed by etching from the front surface side of a p-type nitride semiconductor layer, exposing an n-type nitride semiconductor layer, forming a first and second electrode on the p-type and n-type nitride semiconductor layers respectively, and then cutting into chips. Furthermore, if the insulating substrate is removed or if a conductive substrate is used, etching is not necessary for exposing the aforementioned n-type nitride semiconductor layer, and the second electrode may be formed on the front surface of the substrate and the first electrode may be formed on the back surface of the substrate.

Light Guide

The light guide, which has a receiving end incoming light and a radiation end outgoing light, and has a preferable length, transfers the light radiated from the excitation light source (light emitting element), and guides the light to the wavelength converting member.

The light guide can be freely changed to any length, and the shape can be changed freely, in particular, bending around curves and corners is possible, so the light can be guided to any desired location. Therefore, so long as this property is possible, any material and construction may be used. In particular, guiding the light radiated from the excitation light source to the wavelength converting member without damping is preferable from the viewpoint of energy efficiency.

The light guide may for instance be an extremely fine glass fiber which is used as a transfer path for light when transferring the light, and a combination of materials which have a high refraction index and materials which have a low refraction index, or materials which have high reflectivity may be used. Of these materials, double layer materials with a cross-section where the center region (core) is surrounded by a surrounding region (clad) are preferable, and a material where the refraction index of the core is higher than the refraction index of the clad is more preferable from the viewpoint that a light signal can be transferred without damping. The light guide preferably has a core which occupies a larger area than the clad, from the viewpoint of reducing light density at the end of the light guide. Furthermore, the light guide preferably has a small diameter clad from the viewpoint of preventing light from returning to the light guide. For instance, a core diameter of approximately 1000 µm or less and a clad diameter (including the core diameter) of approximately 1200 µm or less may be exemplified, but a core diameter of approximately 400 µm or less and a clad diameter (including the core diameter) of approximately 450 µm or less is preferable. Specifically, a ratio of core/clad=114/125 (µm) or 72/80 (µm) or the like may be exemplified.

The light guide may be either a monofiber or a multifiber, but a monofiber is preferable. Furthermore, either a single mode fiber or a multimode fiber may be used, but a multimode fiber is preferable.

The material of the light guide is not restricted in particular, and for instance may be quartz glass or plastic or the like. Of these, the core material is preferably constructed from pure silica (pure quartz). Thereby transmission losses can be suppressed.

The shape of the light receiving end and radiation end of the light guide are not restricted in particular, and a variety of shapes are possible, such as a flat surface, convex lens, concave lens, or partially concave and convex shapes. In particular, the core or both the clad and the core at the end of the light guide located at the wavelength converting member and the translucent member to be discussed later may protrude from the light guide end member. Thereby, the light radiation surface area can be made larger at the light guide end and therefore the light density can be further reduced. Incidentally, even if both the core and the clad are exposed in the longitudinal direction, some of the light will be released from the clad, so the light density will be reduced. Exposing a part of the clad or exposing the core from the clad can be accomplished by commonly known methods such as wet or dry etching, or polishing or the like.

Incidentally, the light guide radiation end referred to in this specification does not necessarily narrowly indicate the region where light is radiated at the end, but rather refers to the end of the side where light is radiated. Specifically, if an optical fiber constructed such that the core is internally covered by the clad is used as the light guide for instance, the region where light is radiated is primarily the core, but in this specification, the radiation end refers to the end of the side where light is radiated including both the core and the clad. The same is true for the light receiving end.

Figure 2:
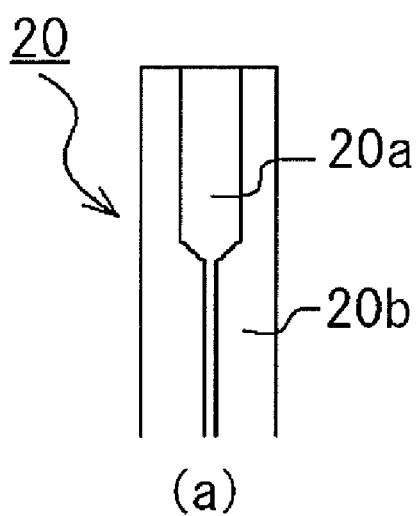
FIG. 2 is a schematic diagram for describing the structure for the end part of the light guide of the light emitting device of the present invention.
Figure 2:
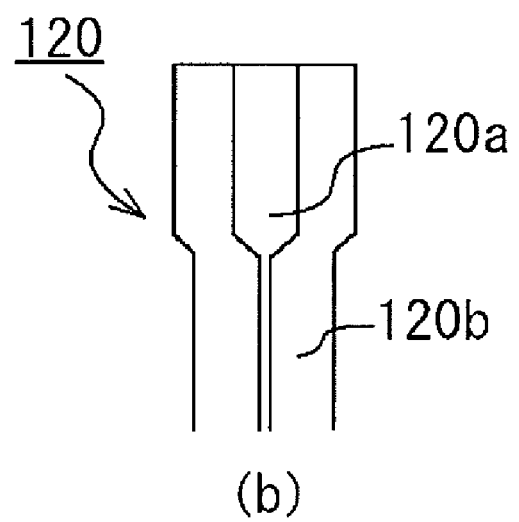

From the viewpoint of reducing light density at the light guide ends, as shown in FIGS. 2(a) and (b), the light guide may have a core diameter at the ends of the light guide 20, 120 which is wider than the core 20a, 120a in the middle region, and for instance, a TEC fiber (clad 20b diameter is fixed), or a taper fiber (clad 120b diameter is tapered) or the like where the core diameter at the ends is approximately 1.05 to 2.0 times the core diameter in the middle region may be exemplified. Thereby degradation of the fiber at the ends of the light guide can be prevented. Furthermore, degradation of the translucent member, the wavelength converting member or the like located at the end of the light guide can be prevented and light can be consistently and efficiently radiated onto the translucent member or the wavelength converting member.

Furthermore, photonic crystal fiber which has one or more air voids or air holes in the core or the clad (Refer to Osamu Toyama, "Photonics Crystal Fiber" Proceedings of 31st Meeting on Lightwave Sensing Technology, LST 31-14, page 89-96, Jun. 6, 2003; Photonics Crystal Fiber DIAGUIDEOR-PCF, Mitsubishi Cable Industries, Ltd., Product Catalog, No. 6-184 (2003.01)), also known as index guiding, photonics bandgap, or hole assisted or the like, may also be used. In order to prevent moisture or the like from permeating into the air holes in photonics crystal fiber, the ends are covered with a predetermined material. Therefore light which has been transferred by the light guide will easily be radiated beyond the width of the core at the end. In any case, the light density at the end of the light guide can be reduced, and therefore the effects of the present invention can more easily be obtained.

Incidentally even normal light guides where the core and/or the clad have a fixed diameter, the ends are preferably covered with a light guide end member, as similar to a photonics crystal fiber or the like, the light will be radiated beyond the width of the core at the light guide end, and the light density can be reduced. The film thickness and the material of the light guide end member are not restricted in particular and any device which can release light without hindrance is acceptable.

Furthermore, from another viewpoint, one end of the light guide which is positioned at the translucent member or wavelength converting member, or in other words, the side which radiates excitation light, has an end surface with a surface area larger than the lateral cross-sectional surface area orthogonal to the longitudinal direction. In other words, all or part of the end surface of the light guide may have a construction with an angle of $X°$ ($0<X°\leq 90$) with regards to the lateral cross section of the light guide (for instance, refer to 20 in FIGS. 3(a) to (g), (r), (t) and (u)), a construction with a curved surface (for instance, refer to 20 in FIGS. 3(h), (j), (l), and (q)), or a construction with a notch in the longitudinal direction (for instance refer to 20 in FIG. 3(s)) or the like. Specifically, the light guide preferably has an angle, curve, or irregular shape or the like such that the surface area of the end surface of one end is 5% or higher, 10% or higher, 15% or higher, 20% or higher, or 30% or higher than the lateral cross-section.

Translucent Member/Wavelength Converting Member

The translucent member transmits the light from an excitation light source (light emitting element). The translucent material may include for instance an inorganic substance such as inorganic glass, yttria sol, alumina sol, or silica sol; or an organic substance such as one or more types of polyolefin resin, polycarbonate resin, polystyrene resin, epoxy resin, acrylic resin, acrylate resin, methacrylic resin (PMMA or the like), urethane resin, polyamide resin, polynorbornene resin, fluoridated resin, silicone resin, modified silicone resin, modified epoxy resin, as well as liquid crystal polymer or the like. These materials preferably have excellent heat durability, light durability, weather durability, and transparency. Of these materials, fluoridated resin and silicone resin (particularly dimethylsiloxane and methyl polysiloxane resins) or the like are preferable, which preferably have durability toward a certain degree of light and heat and formability. Directivity of the light can be controlled by using a translucent member.

The translucent member may include a fluorescent material as a wavelength converting material, pigment or the like as well as a filler.

The wavelength converting member, which comprises a fluorescent material, pigment or the like, absorbs at least part of the excitation light radiated from the excitation light source (light emitting element), converts the wavelength to different wavelength, and can emit light having a emission spectrum such as red, green, blue or the like. In particular, the light emitting device which satisfies both properties of high luminance and high color rendering can be obtained by using fluorescent material.

The wavelength converting member may be formed substantially from fluorescent material alone. In this case, degradation from radiation of high-density excitation light can be kept to a minimum. The wavelength converting member may also include the aforementioned translucent member, and further include filler or the like.

If the translucent member contains wavelength converting material, or the wavelength converting member, the light from the excitation light source (light emitting element) can be combined with light from one or more wavelength converting members, or light from two or more wavelength converting members may be combined in order to create white light. In order to provide good light rendering properties, these are preferably constructed from a material where the average color rendering evaluation value (Ra) of the radiated light is 70 or higher, and more preferably 80 or higher.

Color rendering properties herein refers to the property of a certain light source to control the appearance of the colors of an object which is illuminated by that light source, and good light rendering properties generally refers to achieving close to the appearance of the colors of the object when illuminated by sunlight (Refer to Ohmusha Ltd., "Phosphor Handbook", p 429). Color rendering properties can be improved by using a fluorescent material layer to be discussed later in combination with a light emitting element. Furthermore, the average color rendering evaluation value (Ra) is basically determined by the value of the average color shift when 8 types of color indicators are illuminated by a test light source and a standard light source.

The color tone of the light obtained can be adjusted for instance by combining the light of the three primary colors (blue, green, red). Furthermore, the tone can also be adjusted by combining two colors of light which have a complementary color relationship such as blue and yellow, blue green and red, green and red, or blue-purple and yellow-green. Herein, complementary colors refers to two colors which are on opposite sides of the white point of a color chart. Incidentally, the light of each of the colors used for adjusting the color tone is not all necessarily light which has the wavelength converted by the wavelength converting member, and excitation light obtained from the excitation light source may also be used. Furthermore, with the present invention, the relationship between the color of light and the wavelength is in conformance with JIS Z8110.

The translucent member is transparent to the light from the light emitting element, but part of the light is absorbed without being transmitted, and is converted to heat. Furthermore, if the translucent member includes wavelength converting material, a portion of the light absorbed by the wavelength converting material will be converted to heat without the wavelength being converted. On the other hand, the light guide is fine enough to guide light and be flexible, so concentration of light and the associated heating will be significant at the translucent member or wavelength converting member. Therefore, the present invention is extremely effective for constructions which use a light guide fine enough to be flexible which preferably has a diameter of 3000 μm or less, more preferably 1000 μm or less, even more preferably 400 μm or less and especially 200 μm or less.

Furthermore, the amount of heating of the wavelength converting member caused by light is much larger than the amount of heating of the translucent member, so the present invention is particularly effective when the translucent member contains wavelength converting material.

If the translucent member comprises the wavelength converting material, the wavelength converting material (the fluorescent material or the like) and translucent material (the resin), the weight ratio thereof are mixed to be preferably within a range of approximately 0.1 to 10:1, and more preferably within a range of approximately 0.5 to 10:1, 1 to 3:1, or 1.5 to 2.5:1. However, as will be described later, if the translucent member including the wavelength converting material is formed with a laminate structure, the ratio of fluorescent material or the like and resin in each layer does not necessarily have to be the same. For instance, the material used and the ratios thereof may be appropriately adjusted in consideration of the heat durability, weather durability, and refractive index or the like of the fluorescent material as well as the properties of the actual resin or the like.

Figure 4:
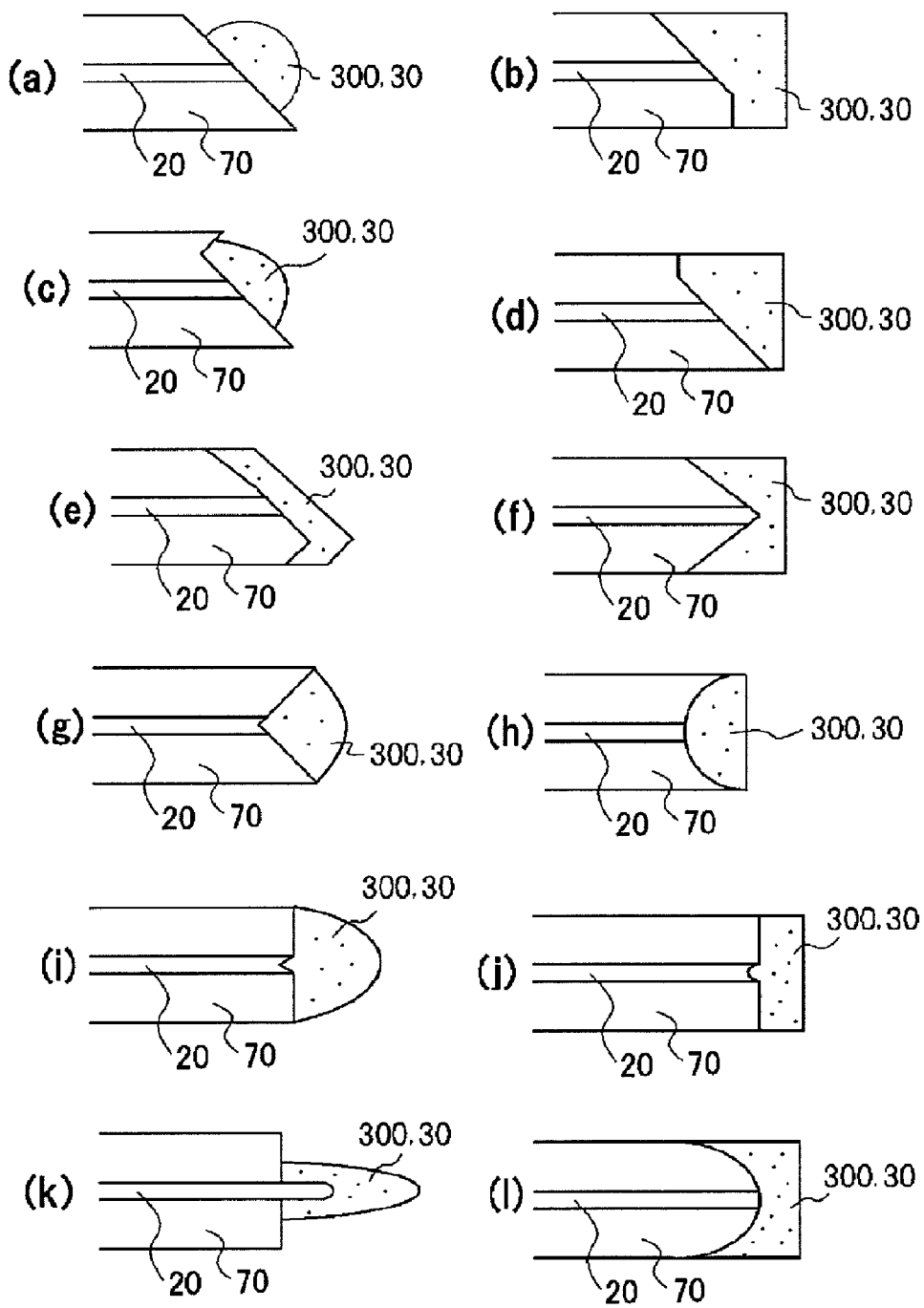
FIG. 4 is a schematic diagram for describing the position of the translucent member and wavelength converting member of the light emitting device of the present invention.

The shape of the translucent member or the wavelength converting member is not restricted in particular, and various shapes such as a convex lens shape or the like are possible. The translucent member or the wavelength converting member is preferably positioned to cover not only the light guide, but also at least a part of the light guide end member which will be described later. For instance, various shapes are possible as shown in FIG. 4 (a)~(l). Incidentally, the contact surface area with the translucent member or the wavelength converting member is preferably as large as possible, such as the translucent member or wavelength converting member covering the light guide end member and the whole end surface of the light guide. Thereby the effects of the present invention can be more easily obtained.

Fluorescent Material

The fluorescent material is not restricted in particular so long as the material is excited by an excitation light from the excitation light source, but preferably at least one type and more preferably a combination of two types of fluorescent materials are used for each excitation light. Examples of various fluorescent materials include:
 (i) alkali earth metal halogen apatite
 (ii) alkali earth metal borate halogen
 (iii) alkali earth metal aluminate
 (iv) oxynitrides or nitrides
 (v) alkali earth silicates and alkali earth nitride silicates
 (vi) sulfides
 (vii) alkali earth thiogallate
 (viii) germinate
 (ix) rare earth aluminate
 (x) rare earth silicate (xi) organic compounds and organic complexes or the like which are primarily activated by lanthanoids such as Eu.

(i) Alkali earth metal halogen apatite fluorescent materials are preferably those which are primarily activated by lanthanoids such as Eu or transition metal elements such as Mn, such as $M_5(PO_4)_3X:RE$ (where M is one or more elements selected from Sr, Ca, Ba, Mg, and Zn; X is one or more elements selected from F, Cl, Br, and I; and RE is Eu and/or Mn).

For instance, calcium chlorapatite (CCA) and barium chlorapatite (BCA) or the like may be exemplified, and specifically, $Ca_{10}(PO_4)_6Cl_2:Eu$, and $(Ba, Ca)_{10}(PO_4)_6Cl_2:Eu$ or the like may be exemplified.

(ii) Examples of alkali earth metal borate halogen fluorescent materials are $M_2B_5O_9X:RE$ (where M, X, and RE are defined as shown above) or the like.

For instance, calcium chlorborate (CCB) or the like may be exemplified, and specifically $Ca_2B_5O_9Cl:Eu$ or the like may be exemplified.

(iii) Examples of alkali earth metal aluminate fluorescent materials are europium activated strontium aluminate (SAE) and europium activated barium magnesium aluminate (BAM), as well as $SrAl_2O_4:R_E$, $Sr_4Al_{14}O_{25}:R_E$, $CaAl_2O_4:R_E$, $BaMg_2Al_{16}O_{27}:R_E$, and $BaMgAl_{10}O_{17}:RE$ (where RE is defined as shown above) or the like.

(iv) Oxynitride fluorescent materials are preferably those primarily activated by rare earth elements, and contain at least one Group II element and at least one Group IV element. Combinations of these elements are not restricted in particular, and examples include those expressed by the following formulations:

$L_xJ_yO_zN_{((2/3)x+(4/3)y-(2/3)z)}:R$ or $L_xJ_yQ_tO_zN_{((2/3)x+(4/3)y+t-(2/3)z)}:R$ (where L is at least one type of Group II elements selected from a group consisting of Be, Mg, Ca, Sr, Ba, and Zn; J is at least one type of Group IV elements selected from a group consisting of C, Si, Ge, Sn, Ti, Zr, and Hf; Q is at least one type of Group III elements selected from a group consisting of B, Al, Ga, and In; R is at least one type of rare earth elements selected from a group consisting of Y, La, Ce, Pr, Nd, Sm, Eu, Gd, Tb, Dy, Ho, Er, Lu, Sc, Yb, and Tm; and $0.5<x<1.5$, $1.5<y<2.5$, $0<t<0.5$, and $1.5<z<2.5$.)

If x, y, and z in the equation are within the aforementioned ranges, high luminance will be obtained, and in particular, oxynitride fluorescent materials where x=1, y=2, and z=2 have higher luminance, and are more preferable. However, the above range is not a restriction and other materials may be used.

Specifically, oxynitride fluorescent materials which use alpha sialon as the base material, oxynitride fluorescent materials which use beta sialon as the base material, and Eu activated calcium aluminum silicon nitride expressed by the formula $CaAlSiN_3:Eu$ or the like may be exemplified.

Nitride fluorescent materials are preferably those activated by the rear rare elements. These fluorescent materials may be nitride fluorescent materials which include at least one type of the aforementioned Group II elements, at least one type of the aforementioned Group IV elements, and N, where B is within a range of 1 to 10,000 ppm. Alternatively, oxygen may also be included in the nitride fluorescent material formulation.

Of the aforementioned materials, nitride fluorescent materials containing Ca and/or Sr, Si, and N, such as calcium silicon nitride (CESN), strontium silicon nitride (SESN), and calcium strontium silicon nitride (SCESN), and particularly those activated by Eu and those where B is within a range of 1 to 10,000 ppm are preferable. A portion of the Eu may be replaced by at least one type of the aforementioned rare earth elements. A portion of the Ca and/or Sr may be replaced by at least one or more of the aforementioned Group II elements. A portion of the Si may be replaced by at least one type of the aforementioned Group IV elements.

Specifically, these nitride fluorescent materials are expressed by the equations $L_xJ_yN_{((2/3)x+(4/3)y)}:R$ or $L_xJ_yO_zN_{((2/3)x+(4/3)y-(2/3)z)}:R$ (where L, J, and R are as defined above; and x, y, and z are such that $0.5 \leq x \leq 3$, $1.5 \leq y \leq 8$, and $0<z \leq 3$), and B is preferably within a range of 1 to 10,000 ppm.

Examples of alkali earth silicates and alkali earth nitride silicates include $M_2Si_5N_8:Eu$, $MSi_7N_{10}:Eu$, $M_{1.8}Si_5O_{0.2}N_8:Eu$, and $M_{0.9}Si_7O_{0.1}N_{10}:Eu$ (where M is as defined above).

(vi) Examples of sulfites include alkali earth sulfides such as CaS:Eu and SrS:Eu or the like as well as $La_2O_2S:Eu$, $Y_2O_2S:Eu$, $Gd_2O_2S:Eu$, ZnS:Eu, ZnS:Mn, ZnCdS:Cu, ZnCdS:Ag/Al, ZnCdS:Cu/Al or the like.

(vii) Examples of alkali earth thiogallate include $MGa_2S_4:Eu$ (where M is as defined above).

(viii) Examples of germinate include 3.5 MgO-0.5 $MgF_2$—$GeO_2$:Mn, and $Zn_2GeO_4$:Mn or the like.

(ix) Rare earth aluminates are preferably those primarily activated by lanthanoid elements such as Ce, for example yttrium aluminum garnet (YAG) and lutetium aluminum garnet (LAG), and specifically includes $Y_3Al_5O_{12}:Ce$, $(Y_{0.8}Gd_{0.2})_3Al_5O_{12}:Ce$, $Y_3(Al_{0.8}Ga_{0.2})_5O_{12}:Ce$, $(Y,Gd)_3(Al,Ga)_5O_{12}:Ce$, $Y_3(Al,Sc)_5O_{12}:Ce$, and $Lu_3Al_5O_{12}:Ce$ (as well as those where all or part of Y is replaced by Lu and those where all or part of the Ce is replaced by Tb) as well as $Tb_3Al_5O_{12}:Ce$, and $Gd_3(Al,Ga)_5O_{12}:Ce$.

(x) Rare earth silicates include $Y_2SiO_5:Ce$, and $Y_2SiO_5:Tb$ or the like.

(xi) Organic compounds and organic complexes are not restricted in particular, and any commonly known material may be used. Materials which are primarily activated by a lanthanoid element such as Eu or the like are preferable, but at least one type selected from a group consisting of the aforementioned rare earth elements as well as Cu, Ag, Au, Cr, Co, Ni, Ti, and Mn may be used in place of or in addition to Eu.

Of these materials, particularly preferable are: (ix) rare earth aluminate fluorescent materials primarily activated by lanthanoid elements such as Ce, specifically YAG type fluorescent materials expressed by the formulations $Y_3Al_5O_{12}:Ce$, and $(Y, Gd)_3Al_5O_{12}:Ce$ or the like (including compounds where all or part of Y is replaced by Lu, and compounds where all or part of the Ce is replaced by Tb); and (iv) oxynitride and nitride fluorescent materials primarily activated by rare earth elements, specifically having a general formula of $L_xJ_yN_{((2/3)x+(4/3)y)}:R$ or $L_xJ_yO_zN_{((2/3)x+(4/3)y-(2/3)z)}:R$ (where L, J, R, x, y, and z are as defined above).

The rare earth aluminate fluorescent materials have high heat durability and therefore can discharge stable light, and also have good wavelength converting efficiency, and can therefore efficiently emit light. Furthermore, nitride fluorescent materials are excited by ultraviolet light and light on the short wavelength side of visible light, and can emit light to the long wavelength side of visible light, and therefore have good color rendering properties. Furthermore, by using a combination of these fluorescent materials, light which has good color rendering properties and which has an average color rendering evaluation value (Ra) of for instance 80 or higher can be obtained.

Furthermore, particularly preferable are:
combinations of (ix) YAG together with at least one type of (i) CCA, (ii) CCB, and (iii) BAM;
combinations of (iii) SAE and (i) CCA:Mn;
combinations of (iii) SAE and (iv) SESN;
combinations of (iii) SAE and (iv) SCESN;
combinations of (iii) SAE and (iv) CESN;
combinations of (i) CCA, (ix) LAG, and (iv) SESN;
combinations of (i) CCA, (ix) LAG, and (iv) SCESN;
combinations of (i) CCA, (ix) LAG, and (iv) CESN;
combinations of (i) CCA, (ix) LAG, and (iv) CaAlSiN$_3$:Eu;
combinations of (ix) LAG, and (iv) SESN;
combinations of (ix) LAG, and (iv) SCESN;
combinations of (ix) LAG, and (iv) CESN; and
combinations of (ix) LAG, and (iv) CaAlSiN$_3$:Eu.

Thus, both good light emitting efficiency and excellent color rendering properties can be achieved.

Furthermore, from another viewpoint, the fluorescent material preferably contains at least some material with good temperature characteristics. Herein, material with good temperature characteristics refers to materials which do not experience a noticeable drop in luminance even when the temperature of the wavelength converting member increases because of laser light illumination, when compared to the luminance of the wavelength converting member at room temperature (25° C.). Specifically, wavelength converting members have a luminance retention rate at 200° C. which is 50% or greater than the luminance retention ratio at room temperature, preferably 55% or greater, 60% or greater, 65% or greater, or 70% or greater. Furthermore, the wavelength converting members have a luminance retention rate at 300° C. which is 30% or greater than the luminance retention ratio at room temperature, preferably 35% or greater, 40% or greater, 45% or greater, or 50% or greater. More preferable are wavelength converting members which have a luminance retention rate at 200° C. which is 50% or greater than the luminance retention ratio at room temperature, preferably 55% or greater, 60% or greater, 65% or greater, or 70% or greater as well as have a luminance retention rate at 300° C. which is 30% or greater than the luminance retention ratio at room temperature, preferably 35% or greater, 40% or greater, 45% or greater, or 50% or greater. The representative examples of such fluorescent material include LAG, BAM, YAG, CCA, SCA, SCESN, SESN, CESN, and CaAlSiN$_3$:Eu or the like. Of these materials, LAG, BAM, BAM:Mn and CaAlSiN$_3$:Eu or the like are preferable. Thereby higher luminance can be achieved.

Besides the aforementioned fluorescent materials, other fluorescent materials which have the same performance and effect may also be used.

As will be discussed later, if two or more types of fluorescent materials are used in combination, each fluorescent material may be used independently, such as added to the light guide end member, or two or more may be combined and added to the light guide end member. In this case, the ratio of the fluorescent material used in each combination can be appropriately adjusted depending on the wavelength of the excitation light source used, the light emitting intensity, and the tone or the like of the light to be obtained.

For instance, if a combination of LAG and SESN, SCESN or CaAlSiN$_3$:Eu is used, the materials will be combined at a weight ratio within a range of approximately 50:1 to 1:50, and more preferably combined at a weight ratio within a range of approximately 30:1 to 1:30, 50:1 to 1:1, or 30:1 to 1:1 respectively. Furthermore if a combination of LAG and CCA and SESN, SCESN or CaAlSiN$_3$:Eu is used, the LAG and CCA will preferably be combined at a weight ratio of approximately 1:10 to 10:1, and more preferably at a weight ratio of approximately 1:5 to 5:1, 10:1 to 1:1, and 5:1 to 1:1. The LAG, and SESN, SCESN, or CaAlSiN$_3$:Eu may be used in combination within the aforementioned ranges.

A concrete form of the wavelength converting member of the present invention preferably uses a combination of LAG (green emitted light) and SCESN or SESN (red emitted light). Therefore, when combined with blue excitation light (light emitting elements which have a light emitting peak within a range of 430 to 500 nm for instance), the three primary colors can be ensured and white emission light can be attained which has good color rendering properties.

A combination of $(Sr, Ca)_5(PO_4)_3Cl$:Eu (blue emitted light) and LAG or $BaSi_2O_2N_2$:Eu (green to yellow emitted light) and SCESN (red emitted light); or a combination of CCA, CCB, or BAM (blue emitted light) and YAG (yellow emitted light); or a combination of CCA, CCB, or BAM or the like (blue emitted light) and LAG (green emitted light) and SCESN (red emitted light) are preferably used, arranged in this order from the light incidence side. Therefore, when combined with a light emitting element which has a light emission peak wavelength within the short wavelength range of visible light from 360 to 420 nm, white emission light with good color rendering properties can be provided.

Incidentally, the desired white light can be achieved from the various color light by changing the formulation ratios of the fluorescent materials used. In particular, if a combination of CCA or the like (blue emitted light) and YAG (yellow emitted light) is used, the weight ratio is preferably approximately 1 to 20:1, more preferably approximately 5 to 10:1, and thereby the light emitting efficiency can be increased.

Furthermore, a combination of LAG (green emitted light) and SESN, SCESN, or CaAlSiN$_3$:Eu (red emitted light) is preferably used. Thereby the light emitting efficiency can be further increased by combining with a light emitting element which has a light emission peak wavelength in the neighborhood of 450 nm (such as 420 to 460 nm).

Furthermore, if a fluorescent material which emits yellow light and a fluorescent material which emits red light are used in combination, and if combined with a light emitting element which has an emission peak wavelength in the neighborhood of 450 nm in the short wavelength band of visible light, the mixed color light which is obtained by combining the excitation light discharged from the light emitting elements and the light release from the fluorescent material will be guided externally as light from the wavelength converting member. This light will white light with a reddish hue.

Furthermore, if a fluorescent material which emits green to yellow light is used, a light emitting element which has an emission peak wavelength in the neighborhood of 450 nm (440 to 470 nm), for instance 445 nm, a short wavelength band of visible light will preferably be used in combination. Therefore the light can be made to be white light by combining the excitation light from the light emitting element with yellow light converted from the excitation light. Therefore, absorption of the light during wavelength conversion can be avoided and the light emitting efficiency can be increased.

For the case where a combination of fluorescent material which emits blue light and fluorescent material which emits yellow light is used, by combining with a light emitting element which has an emission peak wavelength near 375 nm in the ultraviolet light band, the light released will be the white light being released from the wavelength converting member. Ultraviolet light is invisible to human eyes so the only light will be the light released from the fluorescent material with a wavelength converted to visible light.

Furthermore, if (1) a light emitting element which has an emission peak wavelength around 400 nm (for instance 370 to 420 nm) in the short wavelength band of visible light is used in combination with (2) a fluorescent material which emits light closer to blue than the light emitting elements (for instance 440 to 460 nm), (3) a fluorescent material which emits green light (for instance 520 to 540 nm) when excited by blue light, (4) a fluorescent material which emits yellow light (for instance 550 to 580 nm) when excited by blue light, and (5) a fluorescent material which emits red light (for instance 640 to 660 nm) when excited by blue light, then the light release from the wavelength converting member will primarily be white light. In particular, these fluorescent materials are preferably arranged in this order from the side of light incidence. With this combination, the light emitting efficiency can be increased. Furthermore, if a combination of (1), (2), and (4) is used, an even higher light emitting efficiency can be achieved. Furthermore, if a combination of (1) through (3) and (5) is used, the color rendering properties can be improved. Incidentally in these cases, excitation light from the light emitting element was not utilized as a color component of the light, and the white color was obtainable using only light which had been converted by the fluorescent material, so the color temperature and color coordinates were not changed by the light output from the light emitting element, and the white color intensity could be adjusted.

As pigments, dyes and fluorescent dyes such as perylene or the like may be exemplified.

In order to prevent the formation of aggregates and to show maximum light absorbency and light converting efficiency, these fluorescent materials and pigments or the like normally have a particle size in the range of approximately 1 μm to 20 μm, and a range of approximately 2 μm to 8 μm is preferable, and a range of approximately 5 μm to 8 μm is more preferable. Furthermore, by using this type of fluorescent material which has a relatively large particle size, the productivity of the light emitting device can be improved. Herein, the particle size indicates the average particle diameter obtained using the air permeation method. Specifically, in an environment with a temperature of 25° C. and a humidity of 70%, a 1 $cm^3$ test sample is weighed, and after packing into a special tube shaped container, dry air at a fixed pressure is made to flow, and the relative surface area is determined from the pressure differential, and then the average particle size is calculated.

Filler

Filler is a material which can reflect or scatter light which is illuminated from the outside. Thereby the light can be scattered and taken out. Furthermore, the excitation light can uniformly be illuminated onto the fluorescent material or the like, which will have the effect of being good color mixture and reducing color variation. Also, since the degree of viscosity of the translucent member or the wavelength conversion member can be adjusted, adherence to the light guide 20 and the light guide end member can be made easy.

Examples of the filler include silica (fumed silica, sedimentary silica, fused silica, crystalline silica, ultrafine powdered amorphous silica, or silicic anhydride or the like), quartz, titanium dioxide, tin oxide, zinc oxide, tin monoxide, calcium oxide, magnesium oxide, beryllium oxide, aluminum oxide, boric nitride, silica nitride, alumina nitride and other metallic nitrides, SiC and other metallic carbides, calcium carbonate, potassium carbonate, sodium carbonate, magnesium carbonate, barium carbonate and other metallic carbonate, aluminum hydroxide, magnesium hydroxide and other metallic hydroxides, aluminum borate, barium titanate, calcium phosphate, calcium silicate, clay, gypsum, barium sulfate, mica, diatomic earth, white clay, inorganic balloon, talc, lithopone, zeolite, halloysite, fluorescent material, and metal shavings (silver powder) or the like. Furthermore, in order to achieve strength, needle shaped fillers such as potassium titanate, barium silicate, and glass fiber or the like may also be used. Of these, barium titanate, titanium oxide, aluminum oxide, and silicon oxide or the like are preferable.

The particle size of the filler is not restricted in particular, and for instance, filler where the median particle size is greater than 1 μm and less than 5 μm can readily diffusely reflected light from the fluorescent material, and can suppress color variation which easily occurs when using a large diameter fluorescent material or the like. Filler which has a median particle size greater than 1 nm and less than 1 μm will have a slightly lower effect on the light wavelength from the light emitting element, but can increase the viscosity of the coating material such as resin without reducing the luminosity. Therefore fluorescent material or the like can be nearly uniformly dispersed in the resin and be maintained in that condition, and therefore even when using relatively larger diameter fluorescent materials or the like which are difficult to handle, the material can be produced with good yields. When filler with a median particle size greater than 5 μm and less than 100 μm is included in the coating material such as resin, color variation of the light emitting element can be improved because of the effect of light scattering, and the thermal impact durability of the resin can be increased. Incidentally, the filler may have a variety of shapes such as spheres, needles, or flakes, in consideration of the scattering properties and reflection properties or the like.

The filler preferably has approximately the same particle size and/or shape as the fluorescent material or the like. Herein, approximately the same particle size means that the difference between the median particle size of each of the particles is less than 20%, and approximately the same shape means that the difference in the roundness value (roundness=circumferential length of a true circle equal to the projected surface area of the particle/circumferential length of the projection of the particle) which shows the degree of true roundness of each particle is less than 20%. By using this type of filler, the fluorescent material or the like and the filler will mutually interact so that the fluorescent material or the like will be thoroughly dispersed throughout the coating material such as resin, and color variation can be more positively suppressed.

The filler may for instance account for between 0.1 and 80 wt %, and particularly 70 wt % or less, 50 wt % or less, 40 wt % or less, or 30 wt % or less of the total wavelength converting member.

The wavelength converting member or the translucent member is made by mixing the aforementioned fluorescent material or the like together with optional filler, using an appropriate solvent, and can be formed to desired shape by sintering while heating if necessary, by molding which pressurizes, by electrodepositing or the like to preferably form the member which includes substantially the fluorescent material or the like only, optionally the filler. That is, the wavelength converting member or the translucent member may preferably be formed without using an organic substance. Here, including substantially the fluorescent material or the like only means that the fluorescent substance or the like is contained about 95 wt % or more in the wavelength converting member or the translucent member, in other words, the organic substance is contained only about 5 wt % or less in the wavelength converting member or the translucent member. Thereby, even if the light with optical high density is irradiated continuously, degradation resulting from the light can be minimized.

The wavelength converting member or the translucent member is made by mixing the fluorescent material or the like together in a resin which constitutes the translucent member, using an appropriate solvent if necessary, and can be formed to the desired shape by a method such as the potting method, spray method, screen printing method, stencil printing method or the like, as well as plastic molding methods such as the injection method, compression method, transfer method, projection method, extrusion method, lamination method, calendar method, and injection mold method or the like, vacuum coating method, powder spray coating method, electrostatic deposition method, and electric migration deposition method or the like.

The wavelength converting member or the translucent member may be formed as a single layer of one type of fluorescent material or the like, or may be formed as one layer of a uniform mixture of two or more types of fluorescent materials or the like, or may be laminated with two or more layers where each layer contains one type of fluorescent material or the like, or may be laminated with two or more layers where each layer contains a uniform mixture of two or more types of fluorescent materials or the like. Note, for the case where two or more single layers are laminated, the fluorescent material or the like contained in each layer may convert the wavelength of the same wavelength of incident light to the same wavelength of radiated light, or may convert incident light with the same wavelength to radiated light with different wavelengths, but the wavelength converting members preferably convert the wavelength of incident light with different wavelengths to radiation light with the same or different wavelengths. Thereby all of the light which is incident on the wavelength converting member and is to be converted can have the wavelength converted, and more efficient wavelength conversion can be performed.

Figure 5:
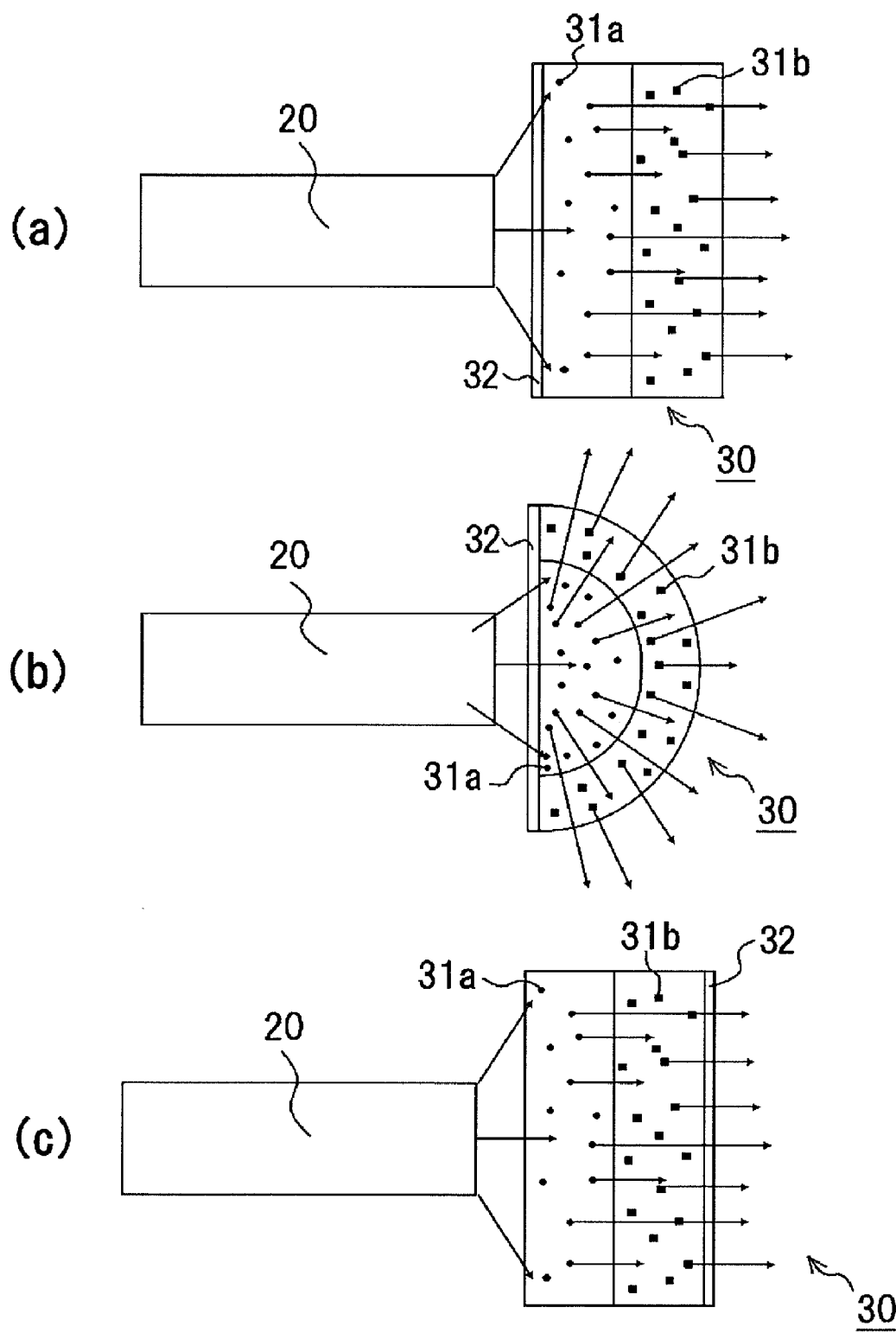
FIG. 5 is a schematic diagram for describing the structure of the wavelength converting member of the light emitting device of the present invention.

As shown in FIG. 5(a), the wavelength converting member or the translucent member may be formed by overlaying sheets containing mutually different types of fluorescent materials 31a, 31b, and as shown in FIG. 5(b), an upper layer containing fluorescent material 31b is overlaid to completely cover a bottom layer which contains a fluorescent material 31a which is different than the fluorescent material 31b. Incidentally, the wavelength converting member 30 preferably has a protruding bowl shape on the radiating side. With this shape, the brightness can be further increased.

The film thickness of the wavelength converting member or the translucent member is not restricted in particular, but can be appropriately adjusted based on the materials used. For instance, if the fluorescent material and resin or the like form a thick film, the conversion efficiency will be increased and as a result the light emitting efficiency can also be increased, but on the other hand, the light emitting efficiency will also be hurt by absorption or the like of the light, so an appropriate film thickness is preferably selected with this in mind.

As shown in FIG. 1, the translucent member 300 (the wavelength converting member 30) may be attached to the end of the light guide 20, or in other words the output region 21 in order to guide the excitation light 1, or may be attached to the connection part between the excitation light source 10 and the light guide 20 which is the radiating part 12 for the excitation light 1. The case of the latter may be used even in locations where the tip end of the light guide will get dirty. Furthermore, replacement of the translucent member or the wavelength converting member will be simplified. Furthermore, productivity can be increased by establishing the translucent member or the wavelength converting members in various locations.

Furthermore, as will be described later, if a plurality of excitation light sources (light emitting device) are used in combination with the first excitation light source and the second excitation light source or the like, the excitation light from each of the excitation light sources will be guided by the light guide and bundled together at the light guide radiating side so that all of the light will be applied to the translucent member including the wavelength converting material by integrating single layers or multiple layers, or partially integrating single layers or multiple layers. Thereby the process of using each of the wavelength converting members or the translucent member can be simplified.

Furthermore, fluorescent material or the like may be included in the core material for instance in a part of the inside of the light guide which will be discussed later.

Lens

With the light emitting device of the present invention, a lens 13 may also be established between the laser elements 11 and the radiating part 12, as shown in FIG. 1 for instance.

The lens may have any configuration so long as the light radiated from the laser element is collected to the incidence region of the light guide, and a plurality of lenses may be arranged in a line between the laser element and the radiating part. The lens may be formed from inorganic glass or plastic or the like, but of these inorganic glass is preferable. The excitation light radiated from the excitation light source can be collected and efficiently guided to the light guide by providing a lens between the excitation light source and the light guide such that the excitation light radiated from the excitation light source can be guided through the lens to the light guide.

Incidentally, the lens may contain material which acts as a wavelength converting member for the fluorescent material. Thereby the wavelength converted excitation light can positively be collected to the radiating part by the lens function and therefore color variation can be eliminated and the cost of manufacturing the wavelength converting member can be held down because the wavelength converting member can be simultaneously manufactured by manufacturing the lens.

Light Guide End Member

With the light emitting device of the present invention, the end of the light guide 20, or in other words the end which is not connected to the excitation light source 10 is preferably supported by a light guide end member normally called a ferrule. The radiating light from the light guide can easily be fixed by this light guide end member. Furthermore, depending on the material and shape thereof, the light emitting efficiency can be increased and the assembly of the light emitting device can be simplified. Therefore, the light guide end member may be constructed using any material and configuration so long as the light guide can be supported.

The light guide end member is preferably formed from a material which has high reflectivity towards the wavelength converted light and/or the excitation light, high refractive index for light, or high thermal conductivity, or a material which provides two or more of these characteristics. Thereby, while raising the luminescence efficiency, heat dissipation, etc. at the end of a light guide, the assembly as the light emitting device becomes easy. Especially, it is desirable to constitute the light emitting device so that the thermal conductivity of a light guide end member may become higher than the thermal conductivity of the translucent member or the wavelength converting member. Thereby, the light guide end member can be made to be able to radiate heat more positively, and the bad influence by the heat of the translucent member or the wavelength converting member can be mitigated.

For instance, a material where reflectivity is 80% or higher at the peak wavelength of the wavelength converted light and/or the excitation light, the refractive index is n:1.4 or higher for light in the 350 to 500 nm range, and/or the thermal conductivity is 0.1 W/m° C. or higher is preferable. Specific examples include Ag, Al, $ZrO_2$, alumina ($Al_2O_3$), aluminum nitride (AlN), borosilicate glass, stainless steel (SUS), carbon, copper, and barium sulfate or the like. Of these materials, if $ZrO_2$ is used the reflectivity will be high and machining for the light guide to pass through will be simple, but if stainless steel is used, the tensile strength can easily be maintained, and therefore forming with $ZrO_2$ or stainless steel (for instance SUS303 or the like) is preferable. Furthermore, alumina has high reflectivity across the whole visible light band and has high thermal conductivity, and is therefore particularly preferable for light emitting devices which emit white emission light.

The light guide end member may for instance have a cylindrical shape in order to cover the outer circumference of the light guide, and various functional films or members which provide various functions to the end surface of the light guide may be integrated with or attached separately thereto, or a cover or cap or the like which covers the end surface of the light guide as well as other functional films or members or the like may be integrated with or separately attached thereto. Incidentally, if the light guide end member has a cylindrical configuration, the diameter is for instance preferably 3 mm or less.

The lateral cross-section of the light guide end member orthogonal to the longitudinal direction may be exposed without modification, but the end surface on the wavelength converting member side of the light guide end member preferably has an angle, curve, or irregular shape or the like so that the surface area is larger than the lateral cross-sectional area orthogonal to the longitudinal direction (Refer to 70 of FIG. 3(i) to (p)). Specifically, all or part of the end surface of the light guide end member may have a construction with a surface at an angle of X° (0≦X°<90) with regards to the lateral cross section (For instance, refer to 70 in FIG. 3(a) to (g), (r) to (u)) or a construction with a curved surface (For instance, refer to 70 in FIG. 3(h), (p) or the like). Thereby, both the effects of increasing the optic output and reducing degradation of the wavelength converting member can be increased.

Furthermore, the light guide end member preferably has a shape with a partially beveled edge on one end. In other words, all or part of the region protruding past the light guide is preferably cut away at the edge of the light guide end member (For instance, refer to 70 in FIGS. 3(b) and (e)).

Thereby the optic output can be further increased, and degradation of the wavelength converting member can be further suppressed. Incidentally, increasing the optic output is thought to be possible because the region which intercepts the light radiated from around the light guide leading end is reduced around the edge of the light guide end member. Suppression of degradation to the wavelength converting member is thought to be because light can efficiently be released to the outside because the region intercepting the light is reduced, and therefore heating is suppressed.

Figure 6:
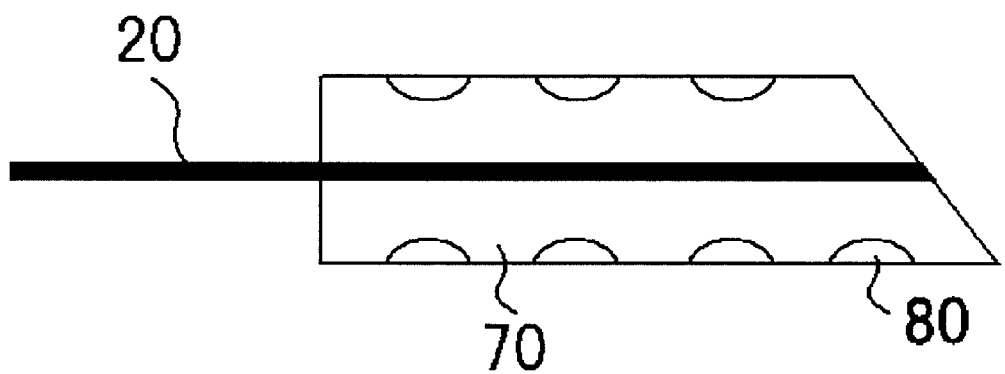
FIG. 6 is a schematic diagram for describing the structure of the light guide end member of the light emitting device of the present invention.

Furthermore, the light guide end member is preferably formed with convex and concave regions (Refer to 80 in FIG. 6) in the side surface as shown in FIG. 6. Thereby, the surface area of the light guide end member can be increased and the heat released from the light guide or the wavelength converting member can be increased.

Figure 3:
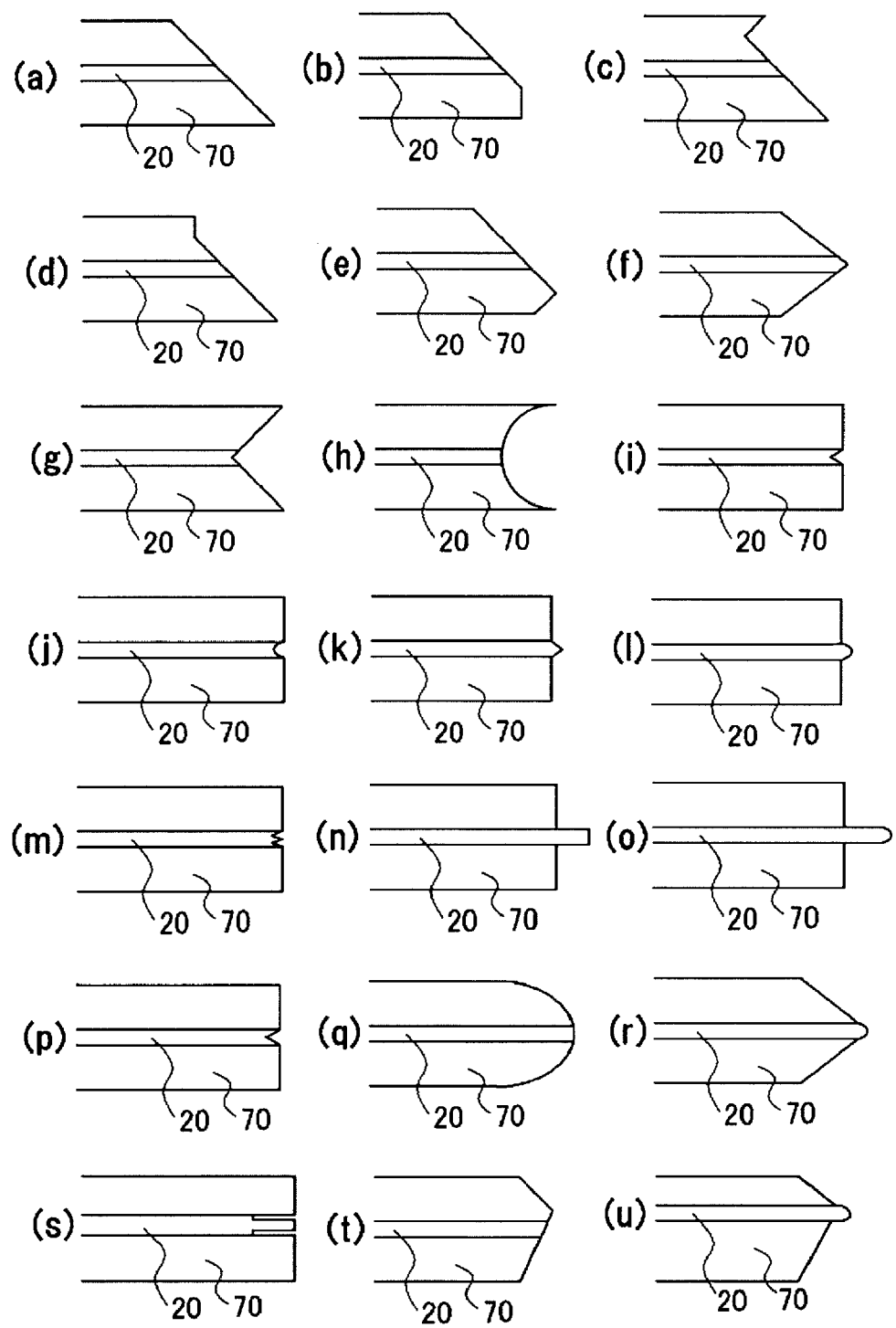
FIG. 3 is a schematic diagram which shows the light guide and light guide end member of the light emitting device of the present invention.

The light guide end member may support the light guide such that the end surface is on the same plane as one end surface of the light guide (For instance, refer to FIGS. 3(a) to (h), (q) and (t)), or the light guide may be supported to protrude from the main end surface of the leading end of the light guide end member (For instance refer to FIGS. 3 (k), (l), (n), (o) and (r)). Furthermore, as shown in FIG. 3(s), a shape is possible where the circumferential region (for instance clad) of the light guide has been removed. Incidentally, if using a light guide where only the core is exposed at the end in the longitudinal direction, a construction where only the core of the light guide protrudes from the leading end of the light guide end member is also acceptable.

Furthermore, from another viewpoint, the light guide end member may also have a construction to form the sidewall of a concave part where at least a part of the radiation end of the light guide forms the bottom. The side wall of the concave part is preferably 0.3 µm or higher, more preferably 0.6 µm or higher, and even more preferably 1.2 µm or higher. Thereby the effects of the present invention can more easily be obtained. The bottom part of the concave part formed by the light guide 20 and the light guide end member 30 is not only flat, but may have a variety of shapes such as curves and points. The height of the side walls of the concave part and the depth of the concave part can be measured using a laser microscope, probe microscope, or a step gauge or the like.

The bottom part of the concave part is not necessarily formed only from the radiation end of the light guide, and only needs to include the radiation end of the light guide. For instance, the bottom part of the concave part may be constructed so that radiation end of the light guide and a part of the light guide end member are on nearly the same plane. Even with this type of construction, the effects of the present invention can be obtained. In order to more effectively obtain the effects of the present invention and have better reproducibility, the bottom part of the concave part is preferably constructed essentially only from the radiation end of the light guide. Furthermore, the sidewalls of the concave part are preferably nearly perpendicular to the end, but an angle is also acceptable.

Figure 7:
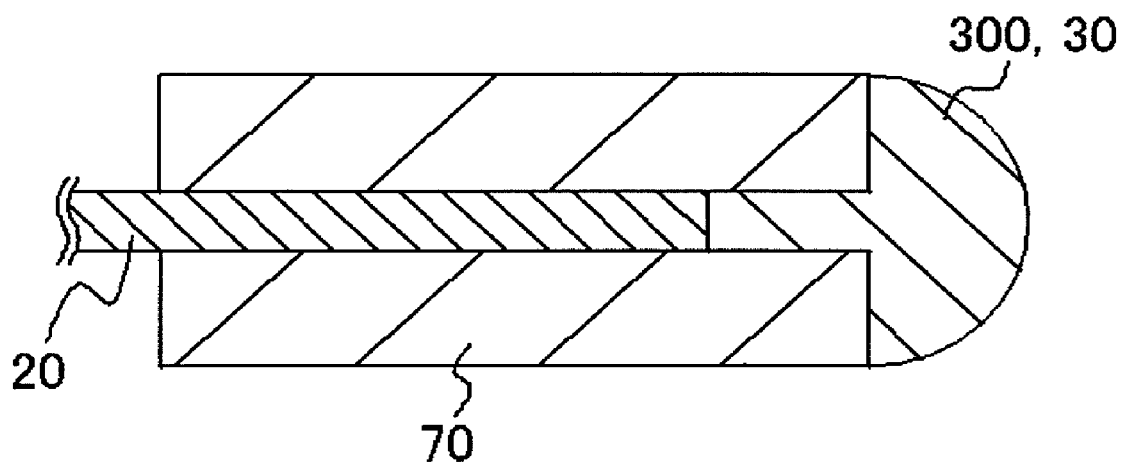
FIG. 7 is a schematic diagram for showing around light emitting end part of the light guide of the light emitting device of the embodiment.

The translucent member extending to the concave region formed by the light guide end member and the light guide preferably extends not only to the concave part, but is also placed on at least a portion of the end of the light guide end member. For instance, as shown in FIG. 7, by placing the translucent member 300 (wavelength converting member 30) along all of the end region of the light guide end member 70, the heat generated in the translucent member can be released not only in the region of the concave part sidewall of the light guide end member, but also from the end of the light guide end member. Incidentally, if a concave part is not formed by the light guide end member and the light guide, even if the light guide end member and the end of the light guide are in the same plane for instance, the heat generated in the translucent member can be released from the end of the light guide end member by placing the translucent member not only at the end of the light guide, but also at least a portion of the end of the light guide end member. In other words, even if the light guide end member and the light guide do not form a concave part, degradation of the translucent member can be reduced. However, as shown in FIG. 7, degradation of the translucent member 300 can be more effectively reduced if the translucent member 300 extends to the concave part, and is positioned on at least a part of the end of the light guide end member 70, and therefore this is preferable.

Incidentally, the light guide end member which forms the sidewall of the concave part and the translucent member should be thermally connected, but the light guide end member and the translucent member do not necessarily have to be directly or perfectly connected. For instance, at the sidewall of the concave part, a construction where the light guide end member and the translucent member are partially contacted, or a construction where the light guide end member and the translucent member are indirectly contacted with for instance a thermally conductive material therebetween are possible. The same applies to the end of the light guide end member and the translucent member.

Furthermore, the light guide end member is not necessarily a single member and maybe constructed from a plurality of members. For instance, the light guide end member may comprise a first member which covers the side surface of the radiation end of the light guide, and a second member which forms the sidewall of the concave part formed with at least a part of the light guide radiation end as the bottom. In this case, the second member preferably is a member with higher thermal conductivity than the first member. Thereby thermal dissipation from the conductive member to the light guide end member can be further increased.

Furthermore, the light guide end member preferably has a mirror for specular reflection at the end surface where the wavelength converting member is located, or may be machined to have a predetermined concave and convex shape for diffuse reflection. Thereby, if excitation light which has once been radiated from the light guide and/or light which has had the wavelength converted returns to the light guide side, the excitation light and the wavelength converted light can effectively be removed again by reflecting using the light guide end member, and therefore the optic output can be increased. Furthermore, if the end surface has a concave and convex shape, the adhesion of the wavelength converting member to the light guide end member can be increased, thermal dissipation of the wavelength converting member can be increased, and peeling or degradation of the wavelength converting member can be prevented. Incidentally, a surface which has specular reflectivity and/or a concave and convex shape preferably is used not only for the light guide end member, but also for the light guide end surface.

Thermally Conductive Transparent Film

With the light emitting device of the present invention, a thermally conductive transparent film is preferably formed in a position which contacts the wavelength converting member. Thereby, if heating of the fluorescent material or the like occurs because extremely high density excitation light is radiated onto the wavelength converting member, the heat can be effectively and promptly dissipated by the thermally conductive transparent film.

For instance, as shown in FIG. 5(a), (b), the thermally conductive transparent film 32 is preferably placed along all or part of the light radiating surface between the light guide 20 and the wavelength converting member 30, and as shown in FIG. 5(c), along all or part of a different light radiating surface of the wavelength converting member than the side where the light guide is present. In particular, the thermally conductive transparent film 32 is preferably formed between the light guide and the wavelength converting member to cover all of the region which radiates excitation light from the light guide. Therefore, when the excitation light from the light guide passes through the thermally conductive translucent member and is introduced to the wavelength converting member, a drop in intensity will not be induced because of the transparent properties, and because of the thermal conductivity properties, heat which is transferred to the translucent member or the wavelength converting member in the region of highest light density can effectively be removed while also releasing heat generated in the translucent member and the wavelength converting member. Specifically, the light guide normally has a light guide end member at the radiation part as will be described later, so a thermally conductive transparent film is placed at the radiation side of the light guide end member.

The thermally conductive transparent film is a single layer or a plurality of layers of at least one type of material including ITO, ZnO, $In_2O$, $SnO_2$, MgO, $Al_2O_3$, $LaF_3$, and $CeF_3$ or the like. Of these materials, a single layer film of ITO, $ZnO_2$, $In_2O_3$, $SnO_3$, or MgO is preferable. Furthermore, these films are preferably formed from monocrystals. Thereby the adhesion or bonding to the translucent member or the wavelength converting member will be better, and thermal mobility to the thermally conductive transparent film can be increased. The appropriate film thickness of this film is, for instance, between 1000 and 10,000 Angstroms.

The thermally conductive transparent film may be formed by a conventionally known method. For instance, a variety of methods may be used including the sputter method, reactive sputter method, vacuum deposition method, ion beam assist vapor deposition method, ion pleating method, laser abrasion method, CVD method, spray method, spincoat method, and dip method, as well as combinations of these methods with heat treatment.

Incidentally, the thermally conductive transparent film has the aforementioned functions, and may also act as a functional film or a functional member or the like which will be described later, so long as the aforementioned functions are also provided.

Functional Membranes and Members

Even if the aforementioned light guide end member is not attached, the light emitting device of the present invention preferably has various functional films or members attached in appropriate locations. Examples of these functional films and members include for instance a wavelength converted light reflecting film, excitation light reflecting film, scatter preventing member, and scattering member or the like.

The wavelength converted light reflecting film prevents wavelength converted light from the wavelength converting member from returning to the excitation light incidence side and also can be used to externally discharge by reflecting light which has returned to the excitation light incidence side. Therefore, the wavelength converted light reflecting film is preferably formed from a material which can transmit only certain wavelengths of light while reflecting certain wavelengths, or in other words, wavelength converted light. Thereby the light which returns to the excitation light incidence side can be reflected and the light emitting efficiency can be increased. Furthermore, the wavelength converted light reflecting film is preferably located at least on the excitation light incidence region of the wavelength converting member.

The excitation light reflecting film can be used to prevent the excitation light from radiating directly to the outside or to prevent the excitation light from leaking to unintended areas. Thereby, excitation light which has passed through the wavelength converting member but was not wavelength converted by the fluorescent material or the like can be returned back to the wavelength converting member in order to increase the light emitting efficiency. Therefore, the excitation light reflecting film is preferably formed from a material which allows transmission of only light of a specific wavelength which has been wavelength converted but reflects excitation light. Furthermore, the excitation light reflecting film is preferably located at least on the wavelength converted light emission region of the wavelength converting member. Thereby radiation of excitation light to the outside can be reduced and the light emitting efficiency can be increased.

The scatter preventing member can be used to prevent excitation light and/or wavelength converted light from scattering in unintended directions. Therefore, the scatter preventing member is preferably constructed with materials and shape which block 90% or more of the excitation light or the wavelength converted light. For instance, at the joint between the light guide and the wavelength converting member, the scatter preventing member may placed between the light guide and the wavelength converting member, or may be placed to surround the boundary region between the light guide and the wavelength converting member, or may be placed to cover the outside surface of the wavelength converting member except for the wavelength converted light emitting region.

The scattering member can be used to increase the light emitting efficiency by causing more of the excitation light to shine on the fluorescent material or the light of the wavelength converting member primarily by scattering the excitation light. Therefore the scattering member is preferably placed between the light radiating port of the light guide and the wavelength converting member. The scattering member may be made from the aforementioned resins which have relatively high refractive index or the aforementioned resins with the aforementioned fillers for instance. Of these materials, a silicone resin is preferable. Thereby the output of light which shines on the wavelength converting member can be reduced and the load on the wavelength converting member per unit area can be reduced in order to increase light emitting efficiency and linearity.

For instance, the film thickness of the scattering member can be appropriately adjusted depending on the core diameter of the light guide, the refractive index and thickness of the optional scattering member, and the size of the wavelength converting member or the like.

Shielding Member

The light emitting device of the present invention may also have a shielding member attached. The shielding member preferably shields 90% or more of the light from the excitation light source. Thereby only light of specific wavelengths may pass through. For instance, when using a light emitting element which radiates ultraviolet light which is harmful to humans, an ultraviolet light absorbing agent or reflecting agent or the like may be added to the wavelength converting member in the light emitting region as a shielding member for shielding the ultraviolet rays. Therefore, emission of ultraviolet rays or the light can be suppressed. Using a reflecting agent is preferable over an absorbing agent from the viewpoint that the light emitting efficiency can be further increased.

Incidentally, the shielding member may also function as the aforementioned excitation light reflecting film or the scatter preventing film or the like so these materials may be used without strictly distinguishing.

Light Emitting Device Mode

Figure 14:
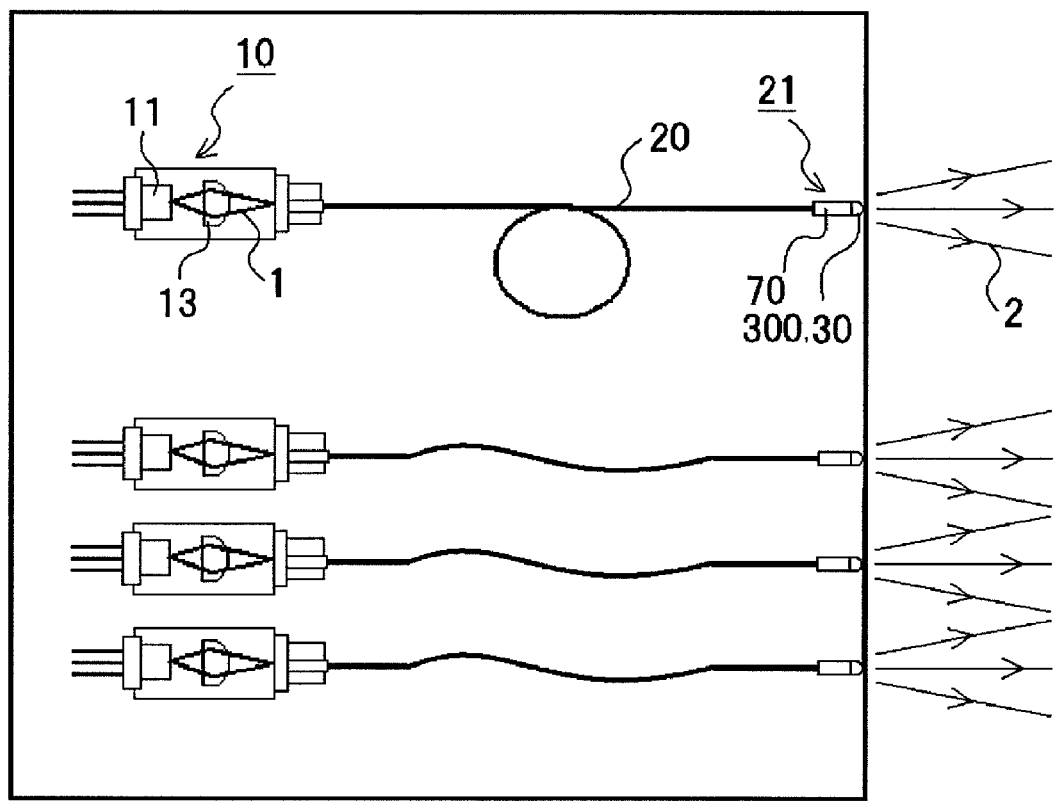
FIG. 14 is a schematic diagram for describing the combination structure for units of the light emitting device of the present invention.

As shown in FIG. 1, the light emitting device of the present invention may be primarily comprised of, for instance, an excitation light source 10 (light emitting element), a light guide 20, and a translucent member 30 (wavelength converting member 30) as a unit, alternately, two or more units may be combined in FIG. 14 to form the light emitting device. The number of units combined can be determined by the color rendering properties and the output. Also, the light emitting device of the present invention may constitute such that the wavelength converting member of each unit may be formed in an integrated fashion.

The light emitting device of the present invention preferably uses units which each have a brightness of approximately 120 lumens/mm$^2$ or higher.

Light Emitting Device Applications

The light emitting device of the present invention with can be used in a variety of applications. For instance, the device may be used as a normal lighting fixture or as automotive lighting (specifically a light source for headlamps and tail lamps or the like), or may be used as a device such as an endoscope for observing inside a living body and performing treatment during observation. Furthermore, the device may also be used as a fiber scope for observing inside extremely narrow or dark spaces such as inside an atomic reactor or inside the space of enclosed artifacts. The device may also be used as a light source for various industrial, construction, and residential applications in members where current leak and heating or the like are to be avoided such as in the chamber of various vacuum devices. In addition, the device may be used as a light emitting device for use in regions where a light source is required or where replacing a light source is difficult.

Therefore, this light emitting device can be used together with an imaging member (in other words an electronic component which converts an optical image to electronic signal (photoreceptor element)), specifically with an imaging element which uses a CCD (charge coupled device) or CMOS (CMOS image sensor), as well as with an image signal processing device which converts an electric signal to an image signal, an indicator for displaying the electronic signal or a measurement value or the like, a display which outputs an image signal and creates an image, and a computer which performs various processes and calculations. In particular, when using an imaging element as an imaging member, the optical image of the object being photographed can easily be handled.

For instance, a photoreceptor element (such as a photo diode or the like) may be established separate from the light emitting device, but may also be established in the light guide end member or around the light guide in close proximity to the laser elements in the excitation light source. Thereby the intensity of light generated from the laser elements can be measured by the photoreceptor element, and when the intensity of light is below a fixed level, the current supplied to the laser element can be adjusted in order to maintain a fixed intensity of light.

The light emitting device of the present invention has high luminance with minimal color variation, extremely good color reproduction, and excellence color rendering properties, and therefore displays excellent effects for use in devices which require brilliant images or the like such as endoscope devices.

Furthermore, the light emitting device of the present invention can also be used for visible light communication. In other words, a wireless environment can be created by using visible light obtained from the aforementioned light emitting device and adding communication functions to the light emitting device. Thereby modulation speeds of several hundred MHz can be achieved because a laser element is used as the excitation light source.

Furthermore, the light emitting device of the present invention can be used as an image display device which displays a color image on an image display unit (screen). The light emitting device of the present invention can generate extremely bright light at high light emitting efficiencies, and can therefore show excellent effects as a light source for end image display device.

Specific examples of the light emitting device of the present invention will be described in detail based on the figures.

Embodiment 1

As shown in FIG. 1, the light emitting device of this embodiment is comprised of an excitation light source 10, a light guide 20, a thermally conductive transparent film (not shown in the figures), and a wavelength converting member 30.

The excitation light source 10 uses a laser diode as a light emitting element 11 which has an emission peak wavelength in the neighborhood of 405 nm. The laser diode is a GaN type semiconductor element.

The light guide 20 has one end which is connected to the light radiating part 12 of the excitation light source 10, and the other end is connected to an output part 21. The light guide 20 is made from quartz, for instance, Si 114 (μm: core diameter)/125 (μm: clad diameter).

The end of the light guide 20 is equipped with an SUS ferrule.

Furthermore, an ITO film with a thickness of 3000 angstroms, which is the end surface of the ferrule, is placed on the whole surface of the light radiating surface of the light guide 30. Incidentally, the ITO film is difficult to form directly on the end surface of the ferrule and the light guide, so the ITO film is formed onto a 150 μm cover glass using the sputter method, which is then placed on the light radiating surface of the light guide 30.

A wavelength converting member 30, essentially made from only fluorescent material, is attached to the light radiating surface side of the ITO film, which is the output part 21.

The fluorescent material was baked by first mixing 2 g of $Ca_{10}(PO_4)_6Cl_2$:Eu which emits blue light and 2 g of a mixture (weight ratio equals 12:88) of ethyl cellulose and terpineol, and then baking at 80° C. for 30 minutes, 200° C. for 10 minutes, and then 500° C. for 1 hour. The film thickness of the wavelength converting member 30 was approximately 500 μm for instance.

A lens 13 for collecting the excitation light 1 from the laser diode was placed in front of the semiconductor light emitting element 10 in the excitation light source 11.

With this light emitting device, the excitation light source was driven at various outputs, and the relative intensity of the light with regards to the optical output was measured.

Figure 8:
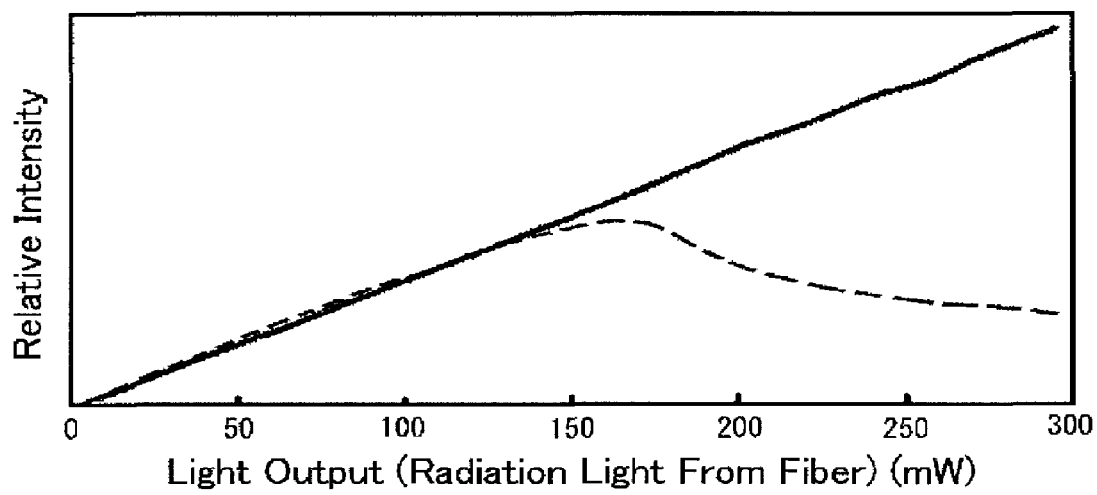
FIG. 8 is a graph showing the relationship between relative intensity and light output for the light emitting device of the embodiment.

The results are shown by the solid line in FIG. 8.

Furthermore, for comparison, a light emitting device was prepared which was identical to the aforementioned light emitting device except that an ITO film was not provided, and this device was similarly driven at various outputs. The results are shown by the broken line in FIG. 8.

According to FIG. 8, the relative intensity of the light with regards to the optic output was confirmed to show good linearity because of the placement of the thermally conductive transparent film.

Furthermore, when the excitation light source had a continuous wave at 100 mW, the temperature of the wavelength converting member was confirmed to be suppressed by the placement of the conductive transparent film for both light emitting devices. Furthermore, by preventing heating of the fluorescent material in the wavelength converting member, degradation of the wavelength converting member was prevented and a longer life for the light emitting device was confirmed.

Incidentally, in order to evaluate the effect of the cover glass on the end surface of the ferrule, a light emitting device was prepared which was identical to the light emitting device of the aforementioned embodiment except that an ITO film and cover glass were not provided. The properties were then measured as described above.

The relative intensity for the optic output was almost identical to the previous light emitting device for comparison, which had only a cover glass.

Embodiment 2

The light emitting devices of this embodiment were essentially identical to the light emitting device of the first embodiment except that LAG, BAM, YAG, SCA, SCESN, SESN, CESN and $CaAlSiN_3$:Eu were each used for the fluorescent material.

When these light emitting devices were similarly evaluated, nearly identical results were obtained for the relative intensity of light compared to the optic output and the device life.

Embodiment 3

The light emitting device of this embodiment was identical to the light emitting device of the first embodiment except that the fluorescent material was made by mixing 10 g of $Ca_{10}(PO_4)_6Cl_2$:Eu, 100 g of isopropyl alcohol, 20 g of alumina sol, and 10 g of acetone, applying a voltage of 50 V, and then drying and using electrodepositing to apply the fluorescent material.

When these light emitting devices were similarly evaluated, nearly identical results were obtained for the relative intensity of light compared to the optic output and the device life.

Embodiment 4

As shown in FIG. 1, the light emitting device of this embodiment is comprised of an excitation light source 10, a light guide 20, a wavelength converting member 30, and a light guide end member 70.

The excitation light source 10 used an LD made from a GaN type semiconductor which has a peak emission wavelength at approximately 405 nm as the light emitting element 11. A lens 13 for collecting excitation light 1 from the LD was placed in front of the LD.

Figure 9:
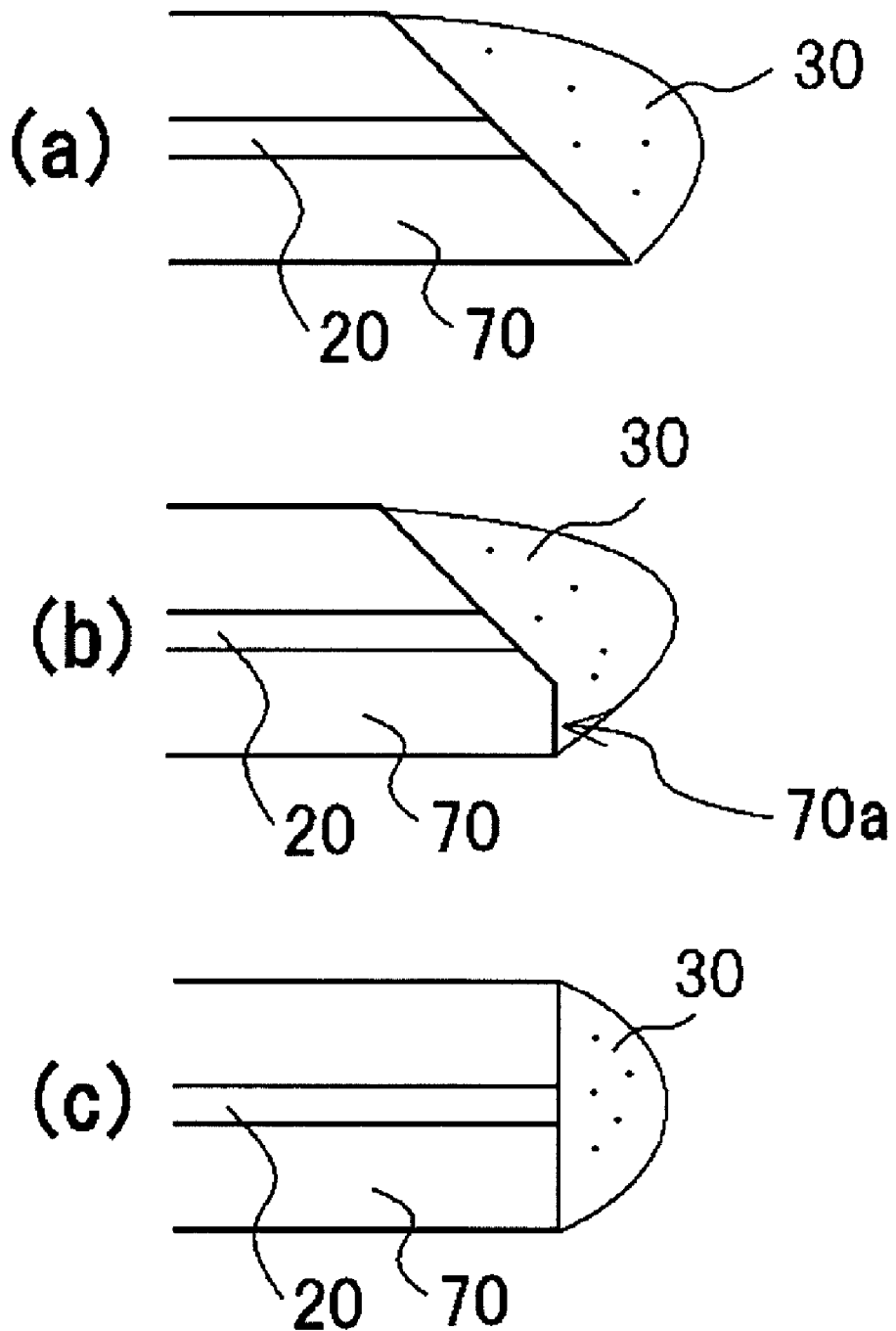
FIG. 9 is a schematic diagram for describing the structure of the light guide end portion of the light emitting device of the embodiment.

The light guide 20 was connected on one end to the light radiating part 12 of the excitation light source 10, and connected on the other end to an output part 21. The light guide 20 is made from quartz Si 114 (µm: core diameter)/125 (µm: clad diameter), and a light guide end member 70 which supports the light guide was made from zirconia ($ZrO_2$) with a diameter of 2.5 mm. Incidentally, as shown in FIG. 9(*b*), the end surface of the light guide 20 and the light guide end member 70 of this embodiment have an 60° angle of inclination with regards to the lateral cross-section which includes the light guide 20, and as another surface, the protruding part of the edge was removed to make an end surface 70*a* which was parallel to the lateral cross-section.

The end surface of the light guide 20 and the light guide end member 70 were formed by first roughly polishing and then finally fine polishing with a #15,000 grain size sheet.

The wavelength converting member 30 was molded in order to uniformly disperse the fluorescent material throughout the resin, and was attached to the output part 21. In other words, a single layer construction wavelength converting member 30 was placed along all of the end surface of both the light guide 20 and the light guide end member 70.

The fluorescent material used 0.9 g of $Ca_{10}(PO_4)_6Cl_2$:Eu (CCA) which emits blue light, and 0.1 g of $Y_3Al_5O_{12}$:Ce (YAG) which emits yellow light. These fluorescent materials were mixed to uniformity in 1.1 g of silicone resin, and a wavelength converting member 30 was manufactured by potting.

Incidentally, for comparison, as shown in FIG. 9(*c*), a light emitting device with the same construction as the above embodiment was prepared except that the end surface of the light guide and the light guide end member had a lateral cross-section which was orthogonal to the longitudinal direction of the light guide.

The excitation light source of this light emitting device was driven using 70 to 280 mA, and the properties of the light emitting device were evaluated.

Figure 10:
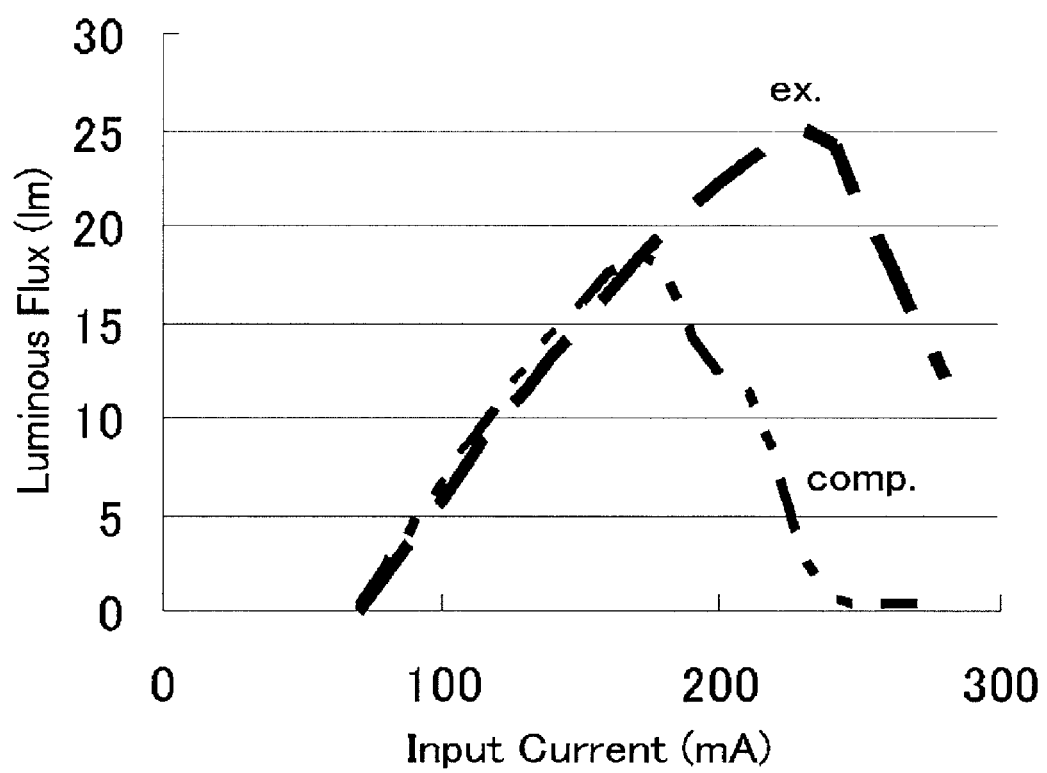
FIGS. 10 to 12 are graphs showing the relationship between luminous flux and input current for the light emitting device of the embodiment.

The results shown in FIG. 10 confirmed that the light emitting device of this embodiment has a peak luminous flux which is approximately 30% higher than the comparative light emitting device, and increased optic output was confirmed.

Incidentally, as shown in FIG. 10, the comparative light emitting device had an input current boundary of approximately 170 mA where the luminous flux dropped off rapidly. The main reason for this is that the wavelength converting member had degraded and changed color. In contrast, with the present embodiment, the luminous flux continued to increase without reaching saturation until the input current was approximately 230 mA. From these results, it was shown that the light emitting device of the present embodiment was more resistant to degradation.

Embodiment 5

The light emitting device of this embodiment was similarly manufactured to be identical to the first embodiment, except that the light guide and the light guide end member had a rough uneven surface made by polishing with a course #200 grain size sheet.

Figure 11:
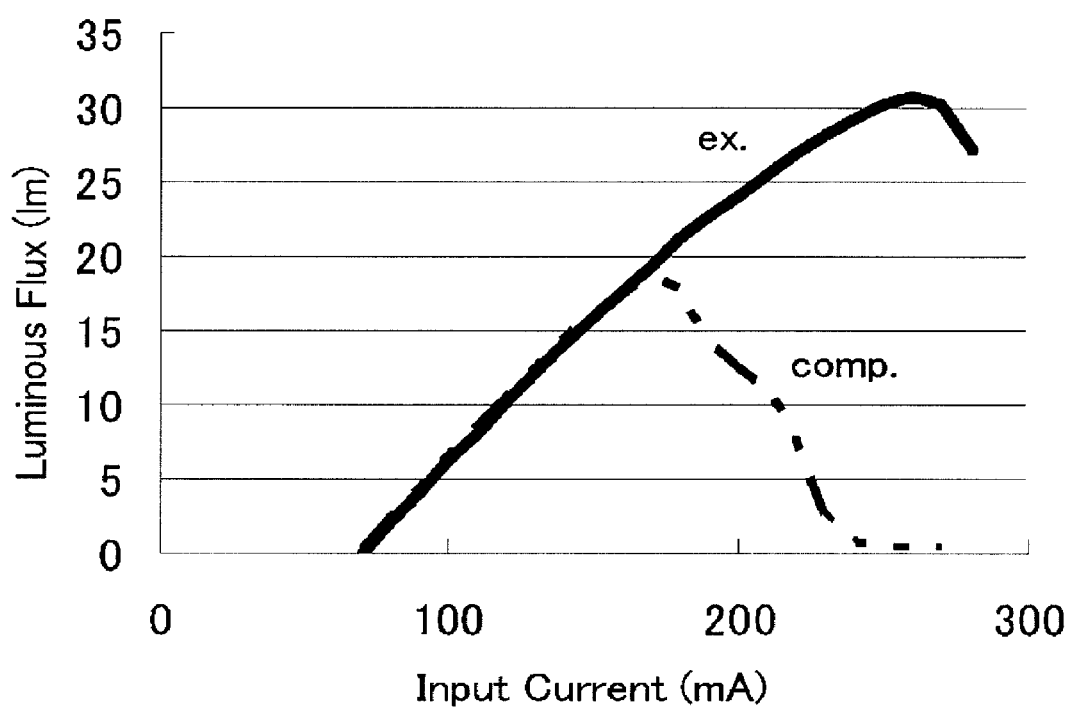

As shown in FIG. 11, when this light emitting device was evaluated similar to the first embodiment, the peak luminous flux was approximately 50% higher than the comparative light emitting device, and the optic output was confirmed to be higher.

By making a rough boundary surface between the light guide/light guide end member and the wavelength converting member, the peak luminous flux was dramatically increased and degradation of the wavelength converting member was reduced. Furthermore, when compared with the sixth embodiment described later which had the same rough surface, the output of this embodiment was superior, so the shape of the embodiment shown in FIG. 9(*b*) was found to be preferable to the configuration of the sixth embodiment shown in FIG. 9(*a*).

Embodiment 6

As shown in FIG. 9(*a*), the light guide 20, light guide end member 70, and the wavelength converting member 30 of this light emitting device were formed to have a simple 60° angled surface without removing the protrusion around the edge. Furthermore, the light guide and the light guide end member are given a rough uneven surface by polishing with a #200 grain size sheet.

Figure 12:
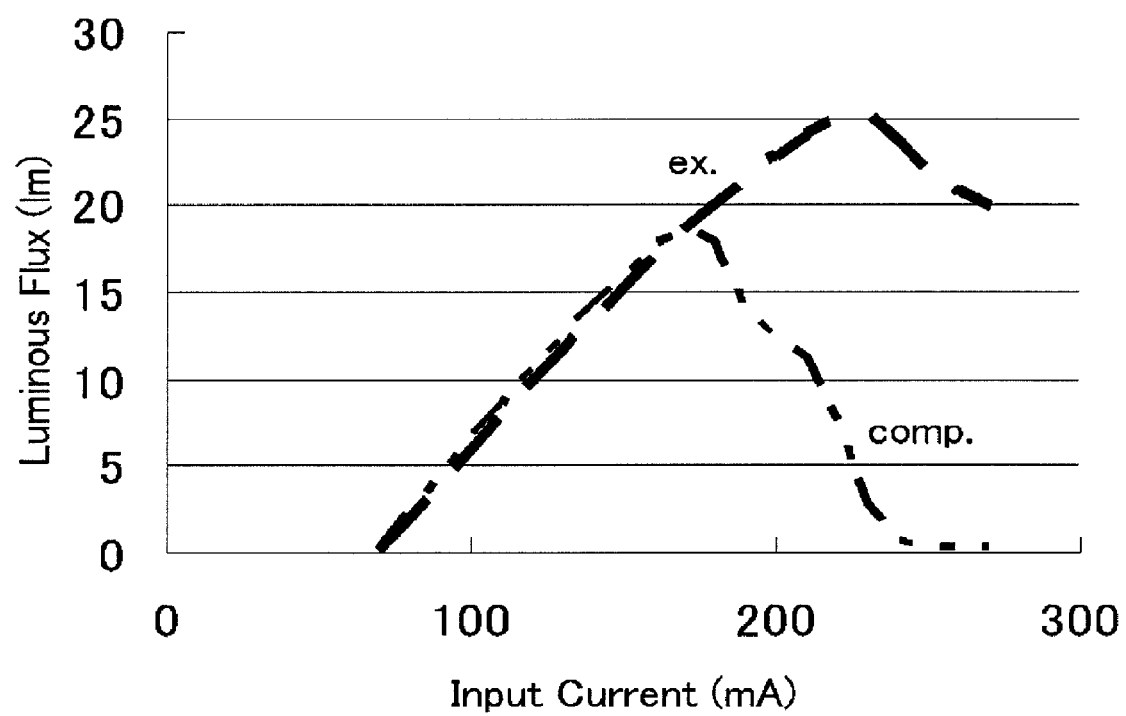

As shown in FIG. 12, when this light emitting device was evaluated similarly to the first embodiment, the peak luminous flux was approximately 30% higher than the comparison light emitting device, and a higher luminance was also confirmed.

Embodiment 7

The light emitting device of this embodiment is primarily comprised of a light emitting element 11, a light guide 20, a light guide end member 70, and a translucent member 300, as shown in FIG. 1. A lens 2 for collecting the light 1 from the light emitting element 11 was provided in front of the light emitting element 11.

The light emitting element 11 was a GaN type semiconductor LD with a peak emission wavelength in the neighborhood of 445 nm; the light guide 20 was a quartz Si type optic fiber 114 (µm: core diameter)/125 (µm: clad diameter); and the light guide end member 70 was made from zirconia ($ZrO_2$) with a diameter of 0.7 mm. Furthermore, the wavelength converting member 30 contained two types of fluorescent material, 0.54 g of $Lu_3Al_5O_{12}$:Ce which emits green light and 0.03 g of $(Sr, Ca)_2Si_5N_8$:Eu in 1.1 g of silicone resin as the translucent member. Incidentally, in this embodiment, zirconia has a thermal conductivity which is three times that of silicone resin.

As shown in FIG. 7, with this embodiment, a concave part was established with all of the radiating end of the light guide 20 forming a single plane bottom part, and the light guide end member 70 forming the sidewalls. When forming the concave part, the light guide 20 and the light guide end member 70 were made from different materials, and can be formed by selectively polishing the light guide 20 using a polishing agent. Herein, an about 1.6 µm concave region was formed in the end of the light guide end member 30.

After forming this concave region, the wavelength converting member 30 was placed by potting onto the radiating end side of the light guide 20 and the light guide end member 70. After potting, vacuum processing was performed in order to more completely mate the wavelength converting member 30 into the concave region.

As a comparative example, a light emitting device was manufactured with the same construction as above except that the light guide 20 and the light guide end member 70 were flat, or in other words, were on the same plane on the radiating end side.

Figure 13:
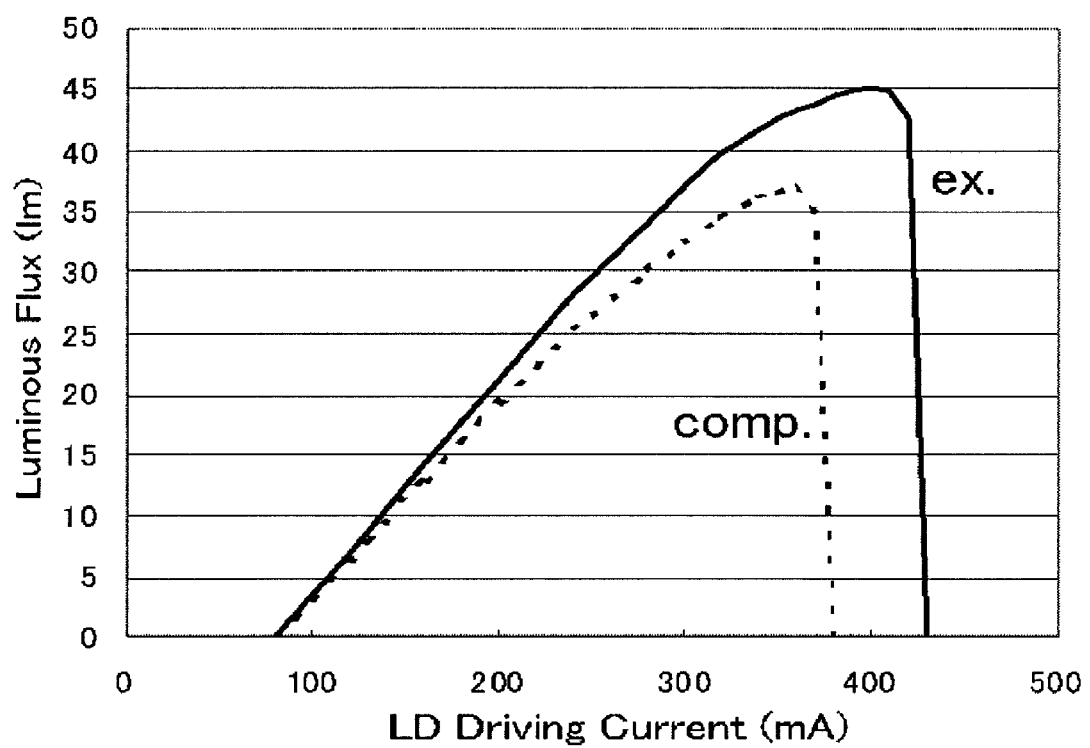
FIG. 13 is a graph showing the relationship between lumen and driving current for the light emitting device of the embodiment.

The LD of both the light emitting device of the present embodiment and the light emitting device of the comparative example were driven using a current of between 80 and 430 mA, and the properties are evaluated in FIG. 13. As shown in FIG. 13, the light emitting device of the present embodiment had a peak luminous flux which was approximately 20% higher than the light emitting device of the comparative example, and the emission output was also confirmed to be higher. According to FIG. 13, the light emitting device of the comparative example had a boundary at a drive current of approximately 370 mA, where the luminous flux dropped off rapidly. The primary reason was because the translucent member was degraded and discolored by heat. In comparison, the present embodiment was confirmed to have increasing luminous flux without reaching saturation until a drive current of approximately 420 mA.

From the above results, it can be seen that the light emitting device of the present embodiment is more resistant to degradation of the translucent member than the comparative example.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A light emitting device comprising:
   a light emitting element;
   a light guide having an end for incoming a light radiated from the light emitting element and an end for outgoing the light, and extending bendably; and
   a translucent material which transmits the light radiated from the light emitting element,
   wherein the translucent material includes a fluorescent material and the fluorescent material is at least one material selected from the group consisting of LAG, BAM, BAM:Mn, $CaAlSiN_3$:Eu.

2. The light emitting device according to claim 1, wherein the fluorescent material has a luminance retention rate at 200° C. which is 50% or greater than the luminance retention ratio at room temperature.

3. The light emitting device according to claim 1, wherein the fluorescent material has a luminance retention rate at 300° C. which is 30% or greater than the luminance retention ratio at room temperature.

4. The light emitting device according to claim 1, wherein the fluorescent material has a particle size in the range of 1 μm to 20 μm.

* * * * *